US008431767B2

(12) United States Patent
Shultz et al.

(10) Patent No.: US 8,431,767 B2
(45) Date of Patent: Apr. 30, 2013

(54) TRANSGENIC NON-HUMAN ANIMAL AND METHODS FOR STEM CELL ENGRAFTMENT

(75) Inventors: Leonard D. Shultz, Bar Harbor, ME (US); Dale L. Greiner, Hubbardston, MA (US)

(73) Assignees: The Jackson Laboratory, Bay Harbor, ME (US); University of Massachusetts Medical School, Worcester, MA (US)

( * ) Notice: Subject to any disclaimer, the term of this patent is extended or adjusted under 35 U.S.C. 154(b) by 143 days.

(21) Appl. No.: 12/942,666

(22) Filed: Nov. 9, 2010

(65) Prior Publication Data

US 2011/0113496 A1 May 12, 2011

Related U.S. Application Data

(60) Provisional application No. 61/259,414, filed on Nov. 9, 2009, provisional application No. 61/291,994, filed on Jan. 4, 2010.

(51) Int. Cl.
*G01N 33/00* (2006.01)
*A01K 67/00* (2006.01)
*A01K 67/033* (2006.01)
*A01K 67/027* (2006.01)

(52) U.S. Cl.
USPC ............... 800/3; 800/13; 800/14; 800/18

(58) Field of Classification Search ............... None
See application file for complete search history.

(56) References Cited

U.S. PATENT DOCUMENTS 7,145,055 B2   12/2006   Ito et al.

OTHER PUBLICATIONS

Bock et al. (1995) Improved engraftment of human hematopoietic cells in severe combined immunodeficient (SCID) mice carrying human cytokine transgenes. The Journal of Experimental Medicine 182: 2037-2043.*
Chen et al. (2000) Porcine stem cell engraftment and seeding of murine thymus with class II+ cells in mice expressing porcine cytokines. Transplantation 69: 2484-2490.*
GenBank Accession No. NP_003985 (2003) KIT ligand isoform a, precursor; mast cell growth factor; stem cell factor precursor (*Homo sapiens*).*
Wall, RJ (1996) Transgenic livestock: Progress and prospects for the future. Theriogenology 45: 57-68.*
Nicolini et al. (2003) NOD/SCID mice engineered to express human IL-3, GM-CSF and Steel factor constitutively mobilize engrafted human progenitors and compromise human stem cell regeneration. Leukemia 18: 341-347.*
Shultz et al. (2005) Human lymphoid and myeloid cell development in NOD/LtSz-scid IL2Rgamma-null mice engrafted with mobilized human hematopoietic stem cells. The Journal of Immunology 174: 6477-6489.*

Abboud, S. et al., Analysis of the Mouse CSF-1 Gene Promoter in a Transgenic Mouse Model, *The Journal of Histochemistry & Cytochemistry*, 51(7): 941-49, 2003.
Bueno, C. at al., Intra-bone marrow transplantation of human CD34+ cells into NOD/LtSz-*scid* IL2ry$^{null}$ mice permits multilineage engraftment without previous irradiation, *Cytotherapy*, 12(1): 5-6, 2010.
Hayakawa, J. et al., Busulfan produces efficient human cell engraftment in NOD/LtSz-*scid IL2Ry null* mice, *Stem Cells*, 27(1): 175-182, Jan. 2009.
Kapur, R. et al., Signaling Through the Interaction of Membrane-Restricted Stem Cell Factor and *c-kit* Receptor Tyrosine Kinase: Genetic Evidence for a Differential Role in Erythropoiesis, *Blood*, 91(3): 879-889, Feb. 1, 1998.
Kapur, R. at al., Overexpression of Human Stem Cell Factor Impairs Melanocyte, Mast Cell, and Thymodyte Development: A Role for Receptor Tyrosine Kinase-Mediated Mitogen Activated Protein Kinase Activation in Cell Differentiation, *Blood*, 90(8): 3018-26, Oct. 15, 1997.
Lowry, P. at al., Improved engraftment of human cord blood stem cells in NOD/LtSz-scid/scid mice after irradiation or multiple-day injections into unirradiated recipients, *Biology of Blood and Marrow Transplantation*, 2: 15-23, 1996.
McBurney, M. et al., Murine PGK-1 Promoter Drives Widespread But Not Uniform Expression in Transgenic Mice, *Developmental Dynamics*, 200; 278-93, 1994.
Majumdar, M. et al., Xenogenic Expression of Human Stem Cell Factor in Transgenic Mice Mimics Codominant c-kit Mutations, *Blood*, 87(8); 3203-11, Apr. 15, 1996.
Martin, F. at al., Primary Structure and Functional Expression of Rat and Human Stem Cell Factor DNAs, *Cell*, 63: 203-211, Oct. 5, 1990.
Michelson, A. et al., Isolation and DNA sequence of a full-length cDNA clone for human X chromosome-encoded phosphoglycerate kinase, *Proc Natl Acad Sci USA*, 80: 472-476, Jan. 1983.
Nicolini, F. et al., NOD/SCID mice engineered to express human IL-3, GM-CSF and Steel factor constitutively mobilize engrafted human progenitors and compromise human stem cell regeneration, *Leukemia*, 18: 341-347, 2004.
Pearson, T. et al., Creation of "Humanized" Mice to Study Human Immunity, *Current Protocols in Immunology*, 15.21.1-15.21.21, Apr. 2008.
Schorpp, M. et al., The human ubiquitin C promoter directs high ubiquitous expression of transgenes in mice, *Nucleic Acids Research*, 24(9): 1787-8, 1996.
The Staff of the Jackson Laboratory. "Chapter 4: The Major Histocompatibility Complex, Minor Histocompatibility Genes, Cellular Antigens, and Other Nonhistocompatibility Congenic Strains." *Handbook on Genetically Standardized Jax® Mice*. Ed. R. Fox, B. Whitman, & L. Neleski. 1997. pp. 57 & 60.

(Continued)

*Primary Examiner* — Anne-Marie Falk
(74) *Attorney, Agent, or Firm* — Gifford, Krass, Sprinkle, Anderson & Citkowski, P.C.

(57) ABSTRACT

Transgenic immunodeficient non-human animals according to embodiments of the present invention are described which include in their genome a nucleic acid encoding xenogeneic Stem Cell Factor operably linked to a promoter. Administration of xenogeneic hematopoetic stem cells to the inventive transgenic animals results in engraftment of the xenogeneic hematopoetic stem cells and xenogeneic leukocytes are produced in the animals, without conditioning such as without conditioning by irradiation and without conditioning by a radiomimetic agent.

16 Claims, 7 Drawing Sheets

OTHER PUBLICATIONS

Watanabe, T. et al., GM-CSF-mobilized peripheral blood CD34+ cells differ from steady-state bone marrow CD34+ cells in adhesion molecule expression, *Bone Marrow Transplantation*, 19: 1175-81, 1997.

Wunderlich, M. et al., A New Immunodeficient Mouse Strain, NOD/SCID IL2Rγ−/− SGM3, Promotes Enhanced Human Hematopoietic Cell Xenografts with a Robust T Cell Component, *51st American Society of Hematology Annual Meeting and Exposition*, Dec. 5-8, 2009 (abstract).

* cited by examiner

TRANSGENIC NON-HUMAN ANIMAL AND METHODS FOR STEM CELL ENGRAFTMENT

REFERENCE TO RELATED APPLICATIONS

This application claims priority to U.S. Provisional Patent Application Ser. Nos. 61/259,414, filed Nov. 9, 2009 and 61/291,994, filed Jan. 4, 2010, the entire content of both of which is incorporated herein by reference.

FIELD OF THE INVENTION

The present invention relates generally to methods and compositions for engraftment of hematopoietic stem cells in an animal. In specific embodiments, the present invention relates to methods and compositions far engraftment of hematopoietic stem cells in an animal without irradiating or other conditioning of the animal prior to administering the hematopoietic stem cells.

BACKGROUND OF THE INVENTION

Immunodeficient mice are used as models of growth and differentiation of normal and abnormal xenogeneic cells. Immunodeficient mice are characterized by one or more of: a lack of functional immune cells, such as T cells and B cells; a DNA repair defect; a defect in the rearrangement of genes encoding antigen-specific receptors on lymphocytes; and a lack of immune functional molecules such as IgM, IgG1, IgG2a, IgG2b, IgG3 and IgA. Immunodeficient mice can be characterized by one or more deficiencies in a gene involved in immune function, such as Rag1 and Rag2 (Oettinger, M. A et al., Science, 248:1517-1523, 1990; and Schatz, D. G. et al., Cell, 59:1035-1048, 1989) Immunodeficient mice may have any of these or other defects which result in abnormal immune function in the mice.

Particularly useful immunodeficient mouse strains are NOD.Cg-Prkdc$^{scid}$ Il2rg$^{tm1Wjl}$/SzJ, commonly referred to as NOD scid gamma (NSG) mice, described in detail in Shultz L D et al, 2005, J. Immunol, 174:6477-89 and NOD.Cg-Rag1tm1Mom Il2rg$^{tm1Wjl}$/SzJ, Shultz L D et al, 2008 Clin Exp Immunol 154(2):270-84 commonly referred to as NRG mice.

While various immunodeficient mouse strains are available, each has drawbacks and limitations in use. In particular, efficient engraftment of xenogeneic stem cells, such as xenogeneic hematopoietic stem cells (HSC), in immunodeficient mice requires irradiation of the recipient mouse or conditioning by radiomimetic drugs such as busulfan. Irradiation of newborn mice results in small, frail mice, and some of the irradiated mice die prematurely. Further, there is concern about the effect of irradiation on hematopoietic development of the treated animals. See, for example, Nielsen et al., Blood, 2007, Vol. 110, No. 3, pp. 1076-1077.

Thus, there is a continuing need for methods and compositions for engraftment of xenogeneic hematopoietic stem cells in immunodeficient mouse strains, particularly without use of irradiation of the recipient immunodeficient mice.

SUMMARY OF THE INVENTION

Transgenic immunodeficient non-human animals according to embodiments of the present invention are described which include in their genome a nucleic acid encoding xenogeneic Stem Cell Factor operably linked to a promoter. Administration of xenogeneic hematopoietic stem cells to the inventive transgenic animals results in engraftment of the xenogeneic hematopoietic stem cells and xenogeneic leukocytes are produced in the animals, without conditioning such as without conditioning by irradiation and without conditioning by radiomimetic agent.

Transgenic immunodeficient non-human animals according to embodiments of the present invention have severe combined immunodeficiency characterized by absence of T cells and lack of B cell function. Transgenic immunodeficient non-human animals according to embodiments of the present invention have an IL2 receptor gamma chain deficiency.

Transgenic immunodeficient mice according to embodiments of the present invention are described which include in their genome a nucleic acid encoding xenogeneic Stem Cell Factor operably linked to a promoter. Administration of xenogeneic hematopoietic stem cells to an inventive transgenic mouse results in engraftment of the xenogeneic hematopoietic stem cells and xenogeneic leukocytes are produced in the mouse, without conditioning such as without conditioning by irradiation and without conditioning by radiomimetic agent.

Transgenic immunodeficient mice according to embodiments of the present invention have severe combined immunodeficiency characterized by absence of mouse T cells and lack of mouse B cell function. Transgenic immunodeficient non-human mice according to embodiments of the present invention have an IL2 receptor gamma chain deficiency.

Transgenic immunodeficient mice according to embodiments of the present invention are described which include in their genome a nucleic acid encoding human Stem Cell Factor operably linked to a promoter. Administration of human hematopoietic stem cells to an inventive transgenic mouse results in engraftment of the human hematopoetic stem cells and human leukocytes are produced in the mouse, without conditioning such as without conditioning by irradiation and without conditioning by radiomimetic agent.

Described herein are embodiments of the present invention where transgenic immunodeficient mice which include in their genome a nucleic acid encoding human Stem Cell Factor operably linked to a promoter and the transgenic immunodeficient mice have the scid mutation. According to embodiments, the inventive transgenic mice are homozygous for the scid mutation.

Transgenic immunodeficient non-human animals according to embodiments of the present invention are described which include in their genome a nucleic acid encoding xenogeneic Stem Cell Factor operably linked to a promoter wherein the xenogeneic Stem Cell Factor is human membrane-associated stem cell factor 248 (SCF$^{248}$), human membrane-associated stem cell factor 220 (SCF$^{220}$) or human soluble stem cell factor (sSCF).

Transgenic immunodeficient non-human animals according to embodiments of the present invention are described which include in their genome a nucleic acid encoding xenogeneic Stem Cell Factor operably linked to a promoter wherein the xenogeneic Stem Cell Factor includes SEQ ID NO. 1, SEQ ID NO. 3, SEQ ID NO. 14, Stem Cell Factor encoded by the complement of a nucleic acid which hybridizes to SEQ ID No. 2 under highly stringent hybridization conditions, Stem Cell Factor encoded by the complement of a nucleic acid which hybridizes to SEQ ID No. 4 under highly stringent hybridization conditions or Stem Cell Factor encoded by the complement of a nucleic acid which hybridizes to SEQ ID No. 15 under highly stringent hybridization conditions.

Provided by embodiments of the present invention are NOD.Cg-Prkdc$^{scid}$ Il2rg$^{tm1Wjl}$/SzJ mice whose genome includes a nucleic acid encoding a xenogeneic Stem Cell Factor operably linked to a promoter. Administration of xenogeneic hematopoetic stem cells to the inventive transgenic NOD.Cg-Prkdc$^{scid}$ Il2rg$^{tm1Wjl}$/SzJ mice whose genome includes a nucleic acid encoding a xenogeneic Stem Cell Factor operably linked to a promoter results in engraftment of the xenogeneic hematopoetic stem cells and xenogeneic leukocytes are produced in the mice, without conditioning such as without conditioning by irradiation and without conditioning by radiomimetic agent.

Transgenic NOD.Cg-Prkdc$^{scid}$ Il2rg$^{tm1Wjl}$/SzJ mice whose genome includes a nucleic acid encoding a xenogeneic Stem Cell Factor operably linked to a promoter according to embodiments of the present invention are described wherein the xenogeneic Stem Cell Factor is human membrane-associated stem cell factor 248 (SCF$^{248}$), human membrane-associated stem cell factor 220 (SCF$^{220}$) or human soluble stem cell factor (sSCF).

Transgenic NOD.Cg-Prkdc$^{scid}$ Il2rg$^{tm1Wjl}$/SzJ mice whose genome includes a nucleic acid encoding a xenogeneic Stem Cell Factor operably linked to a promoter according to embodiments of the present invention are described wherein the xenogeneic Stem Cell Factor includes SEQ ID NO. 1, SEQ ID NO. 3, SEQ ID NO. 14, Stem Cell Factor encoded by the complement of a nucleic acid which hybridizes to SEQ ID No. 2 under highly stringent hybridization conditions, Stem Cell Factor encoded by the complement of a nucleic acid which hybridizes to SEQ ID No. 4 under highly stringent hybridization conditions or Stem Cell Factor encoded by the complement of a nucleic acid which hybridizes to SEQ ID No. 15 under highly stringent hybridization conditions.

Transgenic immunodeficient non-human animals according to embodiments of the present invention are described which include in their genome a nucleic acid encoding xenogeneic Stem Cell Factor operably linked to a promoter wherein the transgenic immunodeficient non-human animals further include xenogeneic haematopoietic stem cells.

Transgenic immunodeficient non-human animals according to embodiments of the present invention are described which include in their genome a nucleic acid encoding xenogeneic Stem Cell Factor operably linked to a promoter wherein the transgenic immunodeficient non-human animals further include xenogeneic leukocytes which have differentiated from administered xenogeneic haematopoietic stem cells.

Methods for xenogeneic stem cell engraftment in an immunodeficient animal having a severe combined immunodeficiency are provided according to embodiments of the present invention which include administering xenogeneic stem cells to the immunodeficient animal; and delivering xenogeneic Stem Cell Factor to the xenogeneic stem cells in the immunodeficient animal.

Methods for xenogeneic stem cell engraftment in a transgenic immunodeficient animal which has included in its genome a nucleic acid encoding xenogeneic Stem Cell Factor operably linked to a promoter are provided according to embodiments of the present invention which include administering xenogeneic hematopoetic stem cells to the transgenic immunodeficient animal.

Methods for xenogeneic stem cell engraftment in a transgenic immunodeficient animal which has included in its genome a nucleic acid encoding xenogeneic Stem Cell Factor operably linked to a promoter are provided according to embodiments of the present invention which include administering xenogeneic hematopoetic stem cells to the transgenic immunodeficient animal without conditioning, such as without conditioning by irradiation and without conditioning by radiomimetic agent.

Methods for xenogeneic stem cell engraftment in a transgenic immunodeficient mouse which has included in its genome a nucleic acid encoding xenogeneic Stem Cell Factor operably linked to a promoter are provided according to embodiments of the present invention which include administering xenogeneic hematopoetic stem cells to the transgenic immunodeficient mouse without conditioning.

Methods for xenogeneic stem cell engraftment in a transgenic immunodeficient mouse heterozygous or homozygous for the scid mutation, wherein the mouse has included in its genome a nucleic acid encoding xenogeneic Stem Cell Factor operably linked to a promoter are provided according to embodiments of the present invention which include administering xenogeneic hematopoetic stem cells to the transgenic immunodeficient mouse without conditioning.

Methods for xenogeneic stem cell engraftment in a transgenic immunodeficient animal which has included in its genome a nucleic acid encoding xenogeneic Stem Cell Factor operably linked to a promoter are provided according to embodiments of the present invention which include administering xenogeneic hematopoetic stem cells to the transgenic immunodeficient animal without conditioning, wherein the xenogeneic stem cells and the xenogeneic Stem Cell Factor are derived from the same species.

Methods for xenogeneic stem cell engraftment in a transgenic immunodeficient animal which has included in its genome a nucleic acid encoding xenogeneic Stem Cell Factor operably linked to a promoter are provided according to embodiments of the present invention which include administering xenogeneic hematopoetic stem cells to the transgenic immunodeficient animal without conditioning, wherein the xenogeneic hematopoetic stem cells and the xenogeneic Stem Cell Factor are human hematopoetic stem cells and human Stem Cell Factor.

Methods for xenogeneic stem cell engraftment in a transgenic immunodeficient animal which has included in its genome a nucleic acid encoding xenogeneic Stem Cell Factor operably linked to a promoter are provided according to embodiments of the present invention which include administering xenogeneic hematopoetic stem cells to the transgenic immunodeficient animal without conditioning, wherein the xenogeneic Stem Cell Factor is human membrane-associated stem cell factor 248 (SCF$^{248}$), human membrane-associated stem cell factor 220 (SCF$^{220}$) or soluble stem cell factor (sSCF).

Combinations of two or more of human membrane-associated stem cell factor 248 (SCF$^{248}$), human membrane-associated stem cell factor 220 (SCF$^{220}$ or soluble stem cell factor (sSCF can be included in animals and methods according to embodiments of the present invention.

Methods for xenogeneic stem cell engraftment in a transgenic immunodeficient animal which has included in its genome a nucleic acid encoding xenogeneic Stem Cell Factor operably linked to a promoter are provided according to embodiments of the present invention which include administering xenogeneic hematopoetic stem cells to the transgenic immunodeficient animal without conditioning, wherein the xenogeneic Stem Cell Factor includes SEQ ID NO. 1, SEQ ID NO. 3, SEQ ID NO. 14, Stem Cell Factor encoded by the complement of a nucleic acid which hybridizes to SEQ ID No. 2 under highly stringent hybridization conditions, Stem Cell Factor encoded by the complement of a nucleic acid which hybridizes to SEQ ID No. 4 under highly stringent hybridization conditions and Stem Cell Factor encoded by the complement of a nucleic acid which hybridizes to SEQ ID No. 15 under highly stringent hybridization conditions.

Methods are provided according to embodiments of the present invention for xenogeneic stem cell engraftment in a transgenic NOD.Cg-Prkdc$^{scid}$ Il2rg$^{tm1Wjl}$/SzJ mouse whose genome comprises a nucleic acid encoding a xenogeneic Stem Cell Factor operably linked to a promoter.

Methods are provided according to embodiments of the present invention for xenogeneic stem cell engraftment in a transgenic NOD.Cg-Prkdc$^{scid}$ Il2rg$^{tm1Wjl}$/SzJ mouse whose genome comprises a nucleic acid encoding a xenogeneic Stem Cell Factor operably linked to a promoter wherein the xenogeneic Stem Cell Factor is human membrane-associated stem cell factor 248 (SCF$^{248}$), human membrane-associated stem cell factor 220 (SCF$^{220}$) or soluble stem cell factor (sSCF).

Methods are provided according to embodiments of the present invention for xenogeneic stem cell engraftment in a transgenic NOD.Cg-Prkdc$^{scid}$ Il2rg$^{tm1Wjl}$/SzJ mouse whose genome comprises a nucleic acid encoding a xenogeneic Stem Cell Factor operably linked to a promoter, wherein the mouse is not irradiated prior to administering the xenogeneic stem cells.

Methods are provided according to embodiments of the present invention for xenogeneic stem cell engraftment in a transgenic NOD.Cg-Prkdc$^{scid}$ Il2rg$^{tm1Wjl}$/SzJ mouse whose genome comprises a nucleic acid encoding a xenogeneic Stem Cell Factor operably linked to a promoter, wherein the mouse is not conditioned by administration of a radiomimetic agent prior to administering the xenogeneic stem cells.

DETAILED DESCRIPTION OF THE INVENTION

Figure 1A:
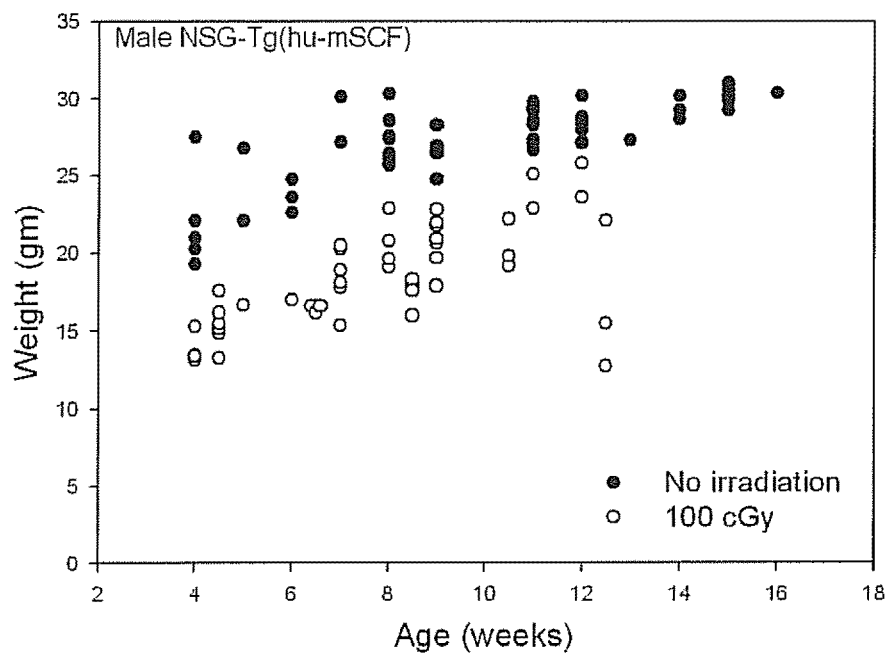
FIG. 1A is a graph showing the weights of unirradiated and 100 cGy irradiated NSG-Tg(hu-mSCF) female mice with age.

Methods for engraftment of xenogeneic hematopoietic stem cells in immunodeficient animals are provided according to embodiments of the present invention which include delivery of xenogeneic stem cell factor (SCF) to the xenogeneic hematopoietic stem cells (HSC) in the immunodeficient animals.

Engraftment of xenogeneic hematopoietic stem cells in immunodeficient animals is characterized by presence of differentiated xenogeneic hematopoietic cells in the animals in which xenogeneic stem cell factor is delivered to xenogeneic hematopoietic stem cells. In particular embodiments, engraftment of xenogeneic hematopoietic stem cells in immunodeficient animals is characterized by greater numbers of differentiated xenogeneic hematopoietic cells in the animals in which xenogeneic stem cell factor is delivered to xenogeneic hematopoietic stem cells compared to appropriate control animals in which xenogeneic stem cell factor is not delivered to xenogeneic hematopoietic stem cells.

Transgenic immunodeficient animals expressing xenogeneic stem cell factor are provided according to embodiments of the present invention.

Methods and transgenic immunodeficient animals provided by embodiments of the present invention have various utilities such as, but not limited to, as models of growth and differentiation of immune cells, in vivo study of immune response and for the testing of agents affecting hematopoietic and immune cell function.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004.

Engraftment of xenogeneic HSC in immunodeficient animals has traditionally required conditioning prior to administration of the HSC, either sub-lethal irradiation of the recipient animal with high frequency electromagnetic radiation, generally using gamma radiation, or treatment with a radiomimetic drug such as busulfan or nitrogen mustard. Conditioning is believed to reduce numbers of host hematopoietic cells, create appropriate microenvironmental factors for engraftment of xenogeneic HSC, and/or create microenvironmental niches for engraftment of xenogeneic HSC. Standard methods for conditioning are known in the art, such as described herein and in J. Hayakawa et al, 2009, Stem Cells, 27(1):175-182. Methods for engraftment of xenogeneic hematopoietic stem cells in immunodeficient animals are provided according to embodiments of the present invention which include delivery of xenogeneic SCF to the xenogeneic HSC in the immunodeficient animals, without irradiating the animals prior to administration of the HSC. Methods for engraftment of xenogeneic hematopoietic stem cells in immunodeficient animals are provided according to embodiments of the present invention which include delivery of xenogeneic SCF to the xenogeneic HSC in the immunodeficient animals, without administering a radiomimetic drug, such as busulfan or nitrogen mustard, to the animals prior to administration of the HSC.

The term "xenogeneic" is used herein with reference to a host cell or organism to indicate that the material referred to as "xenogeneic" is derived from another species than that of the host cell or organism.

The xenogeneic stem cell factor and xenogeneic stem cells may be derived from the same species. Thus, for example, the xenogeneic stem cell factor and xenogeneic stem cells are human SCF and human HSC and the immunodeficient animal is a non-human animal.

The xenogeneic SCF and xenogeneic HSC may be derived from different species as long as the xenogeneic SCF is functionally active with respect to the xenogeneic HSC.

The term "xenogeneic HSC" as used herein refers to multipotent stem cells expressing c-Kit receptor. Examples of multipotent stem cells expressing c-Kit receptor include, but are not limited to, haematopoietic stem cells, also known as hemocytoblasts. C-Kit receptor is well-known in the art, for example as described in Vandenbark G R et al., 1992, Cloning and structural analysis of the human c-kit gene, Oncogene 7(7): 1259-66; and Edling C E, Hallberg B, 2007, c-Kit—a hematopoietic cell essential receptor tyrosine kinase, Int. J. Biochem. Cell Biol. 39(11):1995-8.

Methods for xenogeneic stem cell engraftment in an immunodeficient animal according to embodiments of the present invention include delivering xenogeneic SCF to xenogeneic HSC in an animal having severe combined immune deficiency. The term "severe combined immune deficiency (SCID)" refers to a condition characterized by absence of T cells and lack of B cell function.

Common forms of SCID include: X-linked SCID which is characterized by gamma chain gene mutations in the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+).

Methods for xenogeneic stem cell engraftment in an immunodeficient animal according to embodiments of the present invention include delivering xenogeneic SCF to xenogeneic HSC in a mouse having the severe combined immunodeficiency mutation ($Prkdc^{scid}$), commonly referred to as the scid mutation. The scid mutation is well-known and located on mouse chromosome 16 as described in Bosma, et al., Immunogenetics 29:54-56, 1989. Mice homozygous for the scid mutation are characterized by an absence of functional T cells and B cells, lymphopenia, hypoglobulinemia and a normal hematopoetic microenvironment. The scid mutation can be detected, for example, by detection of markers for the scid mutation using well-known methods.

Methods for xenogeneic stem cell engraftment in an immunodeficient animal according to embodiments of the present invention include delivering xenogeneic SCF to xenogeneic HSC in a mouse having an IL2 receptor gamma chain deficiency in combination with the severe combined immunodeficiency (scid) mutation.

The term "IL2 receptor gamma chain deficiency" refers to decreased IL2 receptor gamma chain. Decreased IL2 receptor gamma chain can be due to gene deletion or mutation. Decreased IL2 receptor gamma chain can be detected, for example, by detection of IL2 receptor gamma chain gene deletion or mutation and/or detection of decreased IL2 receptor gamma chain expression using well-known methods.

SCF delivery is accomplished in any of various ways, including acute delivery such as by injection or chronic delivery such as by implanted infusion pump. According to embodiments of the present invention, SCF delivery is accomplished by expression of a nucleic acid encoding SCF in an immunodeficient animal. According to embodiments of the present invention, a transgenic immunodeficient animal according to embodiments of the present invention expresses a xenogeneic SCF from a nucleic acid encoding the xenogeneic SCF incorporated in some or all of the cells of the animal.

The terms "stem cell factor" and "SCF" are used interchangeably herein to refer to a well-known cytokine that binds to the c-Kit receptor (CD117). SCF is also known as kit ligand, SF, Kitl, KL-1 and other names. Various isoforms of SCF are known including transmembrane and soluble isoforms generated by alternative splicing. Particular isoforms include human membrane-associated stem cell factor 248 ($SCF^{248}$), human membrane-associated stem cell factor 220 ($SCF^{220}$ and soluble stem cell factor (SCF), see Anderson, D. M. et al., 1990, Cell 63, 235; Flannagan, J. G. et al., 1991, Cell 64, 1025; Anderson, D. M. et al., 1991, Cell Growth Differ. 2, 373; Martin, F. H. et al., Cell, 63:203, 1990; Huang E. J. et al., Mol. Biol. Cell, 3:349, 1992; and Huang E. et al., Cell, 63:225, 1990. Amino acid sequences of human soluble SCF, human $SCF^{220}$ and human $SCF^{248}$ along with exemplary nucleic acid sequences encoding human soluble SCF, human $SCF^{220}$ or human $SCF^{248}$ are shown herein. It will be appreciated by those of ordinary skill in the art that, due to the degenerate nature of the genetic code, alternate nucleic acid sequences encode human soluble SCF, human $SCF^{220}$ and human $SCF^{248}$ and variants thereof and that such alternate nucleic acids may be used in compositions and methods described herein.

In addition to these isolated naturally occurring human SCF amino acid sequences, such as human $SCF^{248}$, human $SCF^{220}$ and human sSCF, the term human SCF encompasses variants of human $SCF^{248}$, human $SCF^{220}$ and human sSCF which may be delivered to an immunodeficient animal according to embodiments of methods of the present invention. As used herein, the term "variant" defines either an isolated naturally occurring genetic mutant of a human SCF or a recombinantly prepared variation of a human SCF, each of which contain one or more mutations in its genome compared to the corresponding wild-type human SCF. For example, such mutations can be one or more amino acid substitutions, additions, and/or deletions. The term "valiant" further refers to non-human SCF orthologues.

The term "wild-type" refers to a naturally occurring or unmutated organism, protein or nucleic acid.

In particular embodiments, a variant SCF protein delivered to an immunodeficient animal according to embodiments of the present invention has at least 90%, 91%, 92%, 93%, 94%, 95%, 96%, 97%, 98% or 99% identity to human SCF248, human SCF220 or human sSCF.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions×100%). In one embodiment, the two sequences are the same length.

The determination of percent identity between two sequences can also be accomplished using a mathematical algorithm. A preferred, non limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

Mutations can be introduced using standard molecular biology techniques, such as site-directed mutagenesis and PCR-mediated mutagenesis. One of skill in the art will recognize that one or more amino acid mutations can be introduced without altering the functional properties of human SCF proteins.

Assays for assessment of functional properties of SCF and variants are known in the art as exemplified in Blume-Jensen, P. et al, J. Biol. Chem., 269(34):21793-21802, 1994.

Conservative amino acid substitutions can be made in human SCF proteins to produce human SCF protein variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Human SCF variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

Human SCF variants are encoded by nucleic acids having a high degree of identity with a nucleic acid encoding a wild-type human SCF. The complement of a nucleic acid encoding a human SCF variant specifically hybridizes with a nucleic acid encoding a wild-type human SCF under high stringency conditions.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone.

Nucleic acids encoding SCF or an SCF variant can be isolated or generated recombinantly or synthetically using well-known methodology.

Isolation of xenogeneic HSC, administration of the xenogeneic HSC to a host organism and methods for assessing engraftment thereof are well-known in the art.

Hematopoietic stem cells for administration to an immunodeficient animal can be obtained from any tissue containing HSC such as, but not limited to, umbilical cord blood, bone marrow, GM-CSF-mobilized peripheral blood and fetal liver.

HSC can be administered into newborn animals by administration via various routes, such as, but not limited to, into the heart, liver and/or facial vein. HSC can be administered into adult animals by various routes, such as, but not limited to, administration into the tail vein, into the femur bone marrow cavity or into the spleen. In a further example, the HSC as fetal liver can be engrafted under the renal capsule.

Engraftment of xenogeneic HSC can be assessed by any of various methods, such as, but not limited to, flow cytometric analysis of cells in the animals to which the xenogeneic HSC are administered at one or more time points following the administration of HSC.

Exemplary methods for isolation of xenogeneic HSC, administration of the xenogeneic HSC to a host organism and methods for assessing engraftment thereof are described herein and in T. Pearson et al., Curr. Protoc. Immunol. 81:15.21.1-15.21.21, 2008; Ito, M. et al, Blood 100: 3175-3182; Traggiai, E. et al, Science 304: 104-107; Ishikawa, F. et al, Blood 106: 1565-1573; Shultz, L. D. et al, J. Immunol. 174: 6477-6489; Holyoake T L et al, Exp Hematol., 1999, 27(9):1418-27.

The HSC administered are isolated from an original source material to obtain a population of cells enriched in HSCs. The isolated HSCs may or may not be pure. According to embodiments, HSCs are purified by selection for a cell marker, such as CD34. According to embodiments, administered HSCs are a population of cells in which CD34+ cells constitute about 1-100% of total cells, although a population of cells in which CD34+ cells constitute fewer than 1% of total cells can be used. According to embodiments, administered HSCs are T cell depleted cord blood cells in which CD34+ cells make up about 1-3% of total cells, lineage depleted cord blood cells in which CD34+ cells make up about 50% of total cells, or CD34+ positively selected cells in which CD34+ cells make up about 90% of total cells.

The number of HSCs administered is not considered limiting with regard to generation of a xenogeneic hematopoietic and immune system in an immunodeficient mouse expressing SCF. A single HSC can generate a hematopoietic and immune system. Thus, the number of administered HSCs is generally in the range of $3 \times 10^3$ to $1 \times 10^6$ CD34+ cells where the recipient is a mouse, although more or fewer can be used. For other species, the number of cells can be adjusted if necessary using only routine experimentation.

Engraftment is successful where xenogenic HSCs and cells differentiated from the HSCs in the recipient animal are detected at a time when the majority of any administered non-HSC have degenerated. Detection of differentiated HSC cells can be achieved by detection of xenogeneic DNA in the recipient animal or detection of intact xenogeneic HSCs and cells differentiated from the HSCs, for example. Serial transfer of CD34+ cells into a secondary recipient and engraftment of a xenogeneic hematopoietic system is a further test of HSC engraftment in the primary recipient. Engraftment can be detected by flow cytometry as 0.05% or greater xenogeneic CD45+ cells in the blood, spleen or bone marrow at 10-12 weeks after administration of the HSC.

GM-CSF can be used to mobilize stem cells, for example as described in Watanabe, T., Bone Marrow Transplantation, 19:117501181, 1997. In particular embodiments, a method of the present invention includes delivering xenogeneic SCF to xenogeneic HSC in the immunodeficient animal, particularly a mouse, having the scid mutation or an IL2 receptor gamma chain deficiency in combination with the scid mutation, with the proviso that no stem cell mobilizing agent, such as GM-CSF, is used to mobilize stem cells in the source tissue or animal.

Methods for xenogeneic stem cell engraftment in an immunodeficient animal, are provided which include delivering xenogeneic Stem Cell Factor to xenogeneic stem cells in the immunodeficient animal, with the proviso that immunodeficient animal is not treated with a radiomimetic agent.

Transgenic Non-human Animals

Transgenic immunodeficient non-human animals are provided according to embodiments of the present invention whose genome includes a nucleic acid encoding xenogeneic SCF operably linked to a promoter, wherein the animal expresses the encoded xenogeneic SCF.

Transgenic immunodeficient non-human animals are provided according to embodiments of the present invention whose genome comprises an expression cassette including a nucleic acid encoding xenogeneic SCF, wherein the nucleic acid is operably linked to a promoter and a polyadenylation signal and further contains an intron, wherein the animal expresses the encoded xenogeneic SCF.

Any of various methods can be used to introduce a xenogeneic SCF transgene into immunodeficient animals to produce transgenic immunodeficient animals expressing xenogeneic SCF. Such techniques are well-known in the art and include, but are not limited to, pronuclear microinjection and transformation of embryonic stem cells. Methods for generating transgenic animals that can be used include, but are not limited to, those described in J. P. Sundberg and T. Ichiki, Eds., Genetically Engineered Mice Handbook, CRC Press; 2006; M. H. Hofker and J. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, $3^{rd}$ edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 978047015180; Meyer et al. PNAS USA, vol. 107 (34), 15022-15026.

Transgenic immunodeficient non-human animals having severe combined immunodeficiency or an IL2 receptor gamma chain deficiency in combination with severe combined immunodeficiency are provided according to embodiments of the present invention whose genome comprises a nucleic acid encoding xenogeneic SCF operably linked to a promoter, wherein the animal expresses the encoded xenogeneic SCF.

Generation of a transgenic non-human animal expressing xenogeneic SCF can be achieved by methods such as DNA injection of an expression construct into a preimplantation embryo or by use of stem cells, such as embryonic stem (ES) cells or induced pluripotent stem (iPS) cells.

The terms "expression construct" and "expression cassette" are used herein to refer to a double-stranded recombinant DNA molecule containing a desired nucleic acid xenogeneic SCF coding sequence and containing one or more regulatory elements necessary or desirable for the expression of the operably linked coding sequence. The term "regulatory element" as used herein refers to a nucleotide sequence which controls some aspect of the expression of nucleic acid sequences. Exemplary regulatory elements illustratively include an enhancer, an internal ribosome entry site (IRES), an intron; an origin of replication, a polyadenylation signal (pA), a promoter, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation. Expression constructs can be generated recombinantly or synthetically using well-known methodology.

The term "operably linked" as used herein refers to a nucleic acid in functional relationship with a second nucleic acid.

A regulatory element is included in an expression cassette is a promoter in particular embodiments. The term "promoter" as used herein refers to a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce the desired molecule, and provides a site for specific binding by RNA polymerase and other transcription factors. An included promoter can be a constitutive promoter or can provide inducible expression; and can provide ubiquitous, tissue-specific or cell-type specific expression.

Ubiquitous promoters that can be included in an SCF expression construct include, but are not limited to, a 3-phosphoglycerate kinase (PGK-1) promoter, a beta-actin promoter, a ROSA26 promoter, a heat shock protein 70 (Hsp70) promoter, an EF-1 alpha gene encoding elongation factor 1 alpha (EF1) promoter, an eukaryotic initiation factor 4A (eIF-4A1) promoter, a chloramphenicol acetyltransferase (CAT) promoter and a CMV (cytomegalovirus) promoter.

Tissue-specific promoters that can be included in an SCF expression construct include, but are not limited to, a promoter of a gene expressed in the hematopoietic system, such as an SCF promoter, an IFN-β promoter, a Wiskott-Aldrich syndrome protein (WASP) promoter, a CD45 (also called leukocyte common antigen) promoter, a Flt-1 (fms-like tyrosine kinase, VEGF Receptor 1) promoter, an endoglin (CD105) promoter and an ICAM-2 (Intracellular Adhesion Molecule 2) promoter.

These and other promoters are known in the art as exemplified in Abboud, S. L. et al, J. Histochem & Cytochem., 51(7):941-949, 2003; Schorpp et al, Nucl. Acids Res., 24(9): 1787-1788, 19%; McBurney, M. W. et al, Devel. Dynamics, 200:278-293, 1994; and Majumder, M. et al, Blood, 87(8): 3203-3211, 1996.

In addition to a promoter, one or more enhancer sequences may be included such as, but not limited to, cytomegalovirus (CMV) early enhancer element and an SV40 enhancer element.

Additional included sequences include an intron sequence such as the beta globin intron or a generic intron, a transcription termination sequence, and an mRNA polyadenylation (pA) sequence such as, but not limited to SV40-pA, beta-globin-pA and SCF-pA.

An expression construct may include sequences necessary for amplification in bacterial cells, such as a selection marker (e.g. kanamycin or ampicillin resistance gene) and a replicon.

For methods of DNA injection of an expression construct into a preimplantation embryo, the expression construct is linearized before injection into non-human preimplantation embryos. Preferably the expression construct is injected into fertilized oocytes. Fertilized oocytes are collected from superovulated females the day after mating (0.5 dpc) and injected with the expression construct. The injected oocytes are either cultured overnight or transferred directly into oviducts of 0.5-day p.c. pseudopregnant females. Methods for superovulation, harvesting of oocytes, expression construct injection and embryo transfer are known in the art and described in Manipulating the Mouse Embryo: A Laboratory Manual, 3$^{rd}$ edition, Cold Spring Harbor Laboratory Press; Dec. 15, 2002, ISBN-10: 0879695919. Offspring can be tested for the presence of the transgene by DNA analysis, such as PCR, Southern blot or sequencing. Mice which are carrying the transgene can be tested for protein expression such as by using ELISA or Western blot analysis.

Alternatively the expression construct may be transfected into stem cells (ES cells or iPS cells) using well-known methods, such as electroporation, calcium-phosphate precipitation and lipofection. The cells are screened for transgene integration by DNA analysis, such as PCR, Southern blot or sequencing. Cells with the correct integration can be tested for functional expression tested by protein analysis for SCF using for example ELISA or Western blot analysis.

Mouse ES cells are grown in media optimized for the particular line. Typically ES media contains 15% fetal bovine serum (FBS) or synthetic or semi-synthetic equivalents, 2 mM glutamine, 1 mM Na Pyruvate, 0.1 mM non-essential amino acids, 50 U/ml penicillin and streptomycin, 0.1 mM 2-mercaptoethanol and 1000 U/ml LIF (plus, for some cell lines chemical inhibitors of differentiation) in Dulbecco's Modified Eagle Media (DMEM). A detailed description is known in the art (Tremml et al., 2008, Current Protocols in Stem Cell Biology, Chapter 1:Unit 1C.4. For review of inhibitors of ES cell differentiation, see Buehr, M., et al. (2003). Genesis of embryonic stem cells. Philosophical Transactions of the Royal Society B: Biological Sciences 358, 1397-1402.

Selected cells incorporating the expression construct can be injected into preimplantation embryos. For microinjection, ES or iPS cell are rendered to single cells using a mixture of trypsin and EDTA, followed by resuspension in ES media. Groups of single cells are selected using a finely drawn-out glass needle (20-25 micrometer inside diameter) and introduced through the embryo's zona pellucida and into the blastocysts cavity (blastocoel) using an inverted microscope fitted with micromanipulators. Alternatively to blastocyst injection, stem cells can be injected into early stage embryos (e.g. 2-cell, 4-cell, 8-cell, premorula or morula). Injection may be assisted with a laser or piezo pulses drilled opening the zona pellucida. Approximately 9-10 selected stem cells (ES or iPS cells) are injected per blastocysts, or 8-cell stage embryo, 6-9 stem cells per 4-cell stage embryo, and about 6 stem cells per 2-cell stage embryo. Following stem cell introduction, embryos are allowed to recover for a few hours at 37° C. in 5% $CO_2$, 5% $O_2$ in nitrogen or cultured overnight before transfer into pseudopregnant recipient females. In a further alternative to stem cell injection, stem cells can be aggregated with morula stage embryos. All these methods are well established and can be used to produce stem cell chimeras. For a more detailed description see Manipulating the Mouse Embryo: A Laboratory Manual, 3$^{rd}$ edition (A. Nagy, M. Gertsenstein, K. Vintersten, R. Behringer, Cold Spring Harbor Laboratory Press; Dec. 15, 2002, ISBN-10: 0879695919, Nagy et al., 1990, Development 110, 815-821; U.S. Pat. No. 7,576,259: Method for making genetic modifications, U.S. Pat. No. 7,659,442, U.S. Pat. No. 7,294,754, Kraus et al. 2010, Genesis 48, 394-399).

Pseudopregnant embryo recipients are prepared using methods known in the art. Briefly, fertile female mice between 6-8 weeks of age are mated with vasectomized or sterile males to induce a hormonal state conductive to supporting surgically introduced embryos. At 2.5 days post coitum (dpc) up to 15 of the stem cell containing blastocysts are introduced into the uterine horn very near to the uterus-oviduct junction. For early stage embryos and morula, such embryos are either cultured in vitro into blastocysts or implanted into 0.5 dpc or 1.5 dpc pseudopregnant females according to the embryo stage into the oviduct. Chimeric pups from the implanted embryos are born 16-20 days after the transfer depending on the embryo age at implantation. Chimeric males are selected for breeding. Offspring can be analyzed for transmission of the ES cell genome by coat color and genetic analysis, such as PCR, Southern blot or sequencing. Further the expression of SCF can be analyzed by protein analysis (Western blot, ELISA) or other functional assays. Offspring expressing the transgene are intercrossed to create non-human animals homozygous for the transgene. The transgenic mice are crossed to the immunodeficient mice to create a congenic immunodeficient strain with the xenogeneic SCF transgene.

Figure 5A:
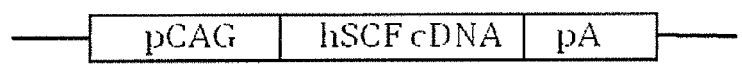
FIG. 5A is a schematic representation of a DNA construct containing the CAG promoter, which is a combination of the cytomegalovirus (CMV) early enhancer element and chicken beta-actin promoter followed by sequences encoding for the human SCF protein and a transcription termination and mRNA polyadenylation (pA) signal; sequence lengths are not drawn to scale.
Figure 5B:
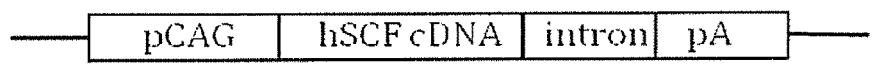
FIG. 5B is a schematic representation of a DNA construct containing the CAG promoter, which is a combination of the cytomegalovirus (CMV) early enhancer element and chicken beta-actin promoter and intron 1 followed by sequences encoding for the human SCF protein, an intron (e.g. rabbit beta-globin intron) and a transcription termination and mRNA polyadenylation (pA) signal; sequence lengths are not drawn to scale.
Figure 5C:
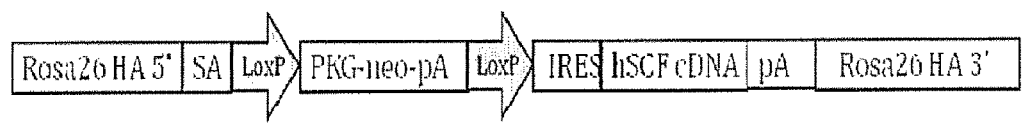
FIG. 5C is a schematic representation of a DNA construct for introducing the hSCF cDNA by gene targeting into the mouse Gt(ROSA)26Sor locus (Rosa26). Homology arms ("Rosa26 HA5'" and "Rosa26 HA3'") to the mouse Gt(ROSA)26Sor locus are shown flanking the construct. The construct includes 5' to 3' a splice acceptor site (SA), a loxP site, the promoter of the mouse Pgk1 (PGK) gene operably linked to the neomycin phosphotransferase coding sequence (neo), a transcription termination and mRNA polyadenylation (pA) signal, followed by a loxP site, followed by an internal ribosome entry site (IRES) and a sequence that codes for the human SCF protein, followed by a transcription termination and mRNA polyadenylation (pA) signal; sequence lengths are not drawn to scale.

Alternatively the transgene is targeted into a specific locus of the stem cell genome which is known to result in reliable expression, such as the Hprt or the Rosa26 locus. For targeted transgenics, a targeting construct is made using recombinant DNA techniques and includes 5' and 3' sequences which are homologous to the stem cell endogenous gene. The targeting construct further includes a selectable marker such as neomycin phosphotransferase, hygromycin or puromycin, a nucleic acid encoding xenogeneic SCF and a polyadenylation signal. To insure correct transcription and translation of the nucleic acid encoding xenogeneic SCF, the nucleic acid encoding xenogeneic SCF is either in frame with the endogenous gene locus, or a splice acceptor site and internal ribosome entry site (IRES) sequences are included. For example see FIG. 5C. Such a targeting construct is transfected into stem cells and the stem cells are screened to detect the homologous recombination event using PCR, Southern blot or sequencing analysis. Cells with the correct homologous recombination event can be further analyzed for transgene expression by protein analysis, such as ELISA or Western blot analysis. If desired, the selectable marker can be removed by treating the stem cells with Cre recombinase. After Cre recombinase treatment the cells are analyzed for the presence of the nucleic acid encoding xenogeneic SCF. Cells with the correct genomic event will be selected and injected into preimplantation embryos as described above. Chimeric males are selected for breeding. Offspring can be analyzed for transmission of the ES cell genome by coat color and genetic analysis, such as PCR, Southern blot or sequencing and can be tested for SCF protein expression such as by protein analysis (Western blot, ELISA) or other functional assays. Offspring expressing the by protein analysis (Western blot, ELISA) or other functional assays are intercrossed to create non-human animals homozygous for the transgene. The transgenic mice are crossed to the immunodeficient mice to create a congenic immunodeficient strain with the xenogeneic SCF transgene.

Embodiments of the invention provide transgenic animals that include a xenogeneic SCF transgene in substantially all of their cells, as well as transgenic animals that include a xenogeneic SCF transgene in some, but not all their cells. One or multiple copies (such as concatamers) of the xenogeneic SCF transgene may be integrated into the genome of the cells of the transgenic animals.

Transgenic animals of the present invention are preferably non-human mammals, particularly rodents, such as mice, rats or guinea pigs.

Transgenic immunodeficient mice having the scid mutation or an IL2 receptor gamma chain deficiency in combination with the scid mutation are provided according to embodiments of the present invention whose genome comprises a nucleic acid encoding xenogeneic SCF operably linked to a promoter, wherein the animal expresses the encoded xenogeneic SCF.

Transgenic NOD scid gamma mice expressing human SCF$^{248}$, human SCF$^{220}$ and/or human sSCF are provided according to embodiments of the present invention.

The terms "NOD scid gamma" and "NSG" are used interchangeably herein to refer to a well-known immunodeficient mouse strain NOD.Cg-Prkdc$^{scid}$ Il2rg$^{tm1Wjl}$/SzJ. NSG mice combine multiple immune deficits from the NOD/ShiLtJ background, the severe combined immune deficiency (scid) mutation, and a complete knockout of the interleukin-2 receptor gamma chain. As a result, NSG mice lack mature T, B and NK cells, and are deficient in cytokine signaling. NSG mice are characterized by lack of IL2R-γ (gamma c) expression, no detectable serum immunoglobulin, no hemolytic complement, no mature T lymphocytes, and no mature natural killer cells.

Transgenic immunodeficient mice expressing human SCF$^{248}$, human SCF$^{220}$ and/or human sSCF are generated by introduction of an expression cassette including a nucleic acid encoding an SCF protein operably linked to a promoter into cells to express the SCF protein in the transgenic animal.

An expression cassette can be introduced into the pronuclei of fertilized eggs of the desired immunodeficient mouse strain, such as NSG for example. The microinjected eggs are either transferred the same day into oviducts of 0.5-day post coitus (p.c.) pseudopregnant females or cultured overnight and transferred the next day into oviducts of 0.5-day p.c. pseudopregnant females. The resulting pups are tested for presence of the transgene and expressed human SCF protein. The nucleic acid can be stably integrated into the chromosomal genome of a cell or maintained as a stable episome.

In a further embodiment, an expression cassette can be introduced into the pronuclei of fertilized eggs of NOD-SCID (NOD.CB17-Prkdc$^{scid}$/J). The microinjected eggs are either transferred the same day into oviducts of 0.5-day p.c. pseudopregnant females or cultured overnight and transferred the next day into oviducts of 0.5-day p.c. pseudopregnant female. The resulting pups are tested for presence of the transgene and those positive for the transgene can be crossed with NSG or NRG.

The terms "expressing" and "expresses" refer to transcription of a gene to produce a corresponding mRNA and/or translation of the mRNA to produce the corresponding protein.

Embodiments of inventive compositions and methods are illustrated in the following examples. These examples are provided for illustrative purposes and are not considered limitations on the scope of inventive compositions and methods.

EXAMPLES

Generation of Transgenic SCF$^{220}$ Mice

In this example, transgenic immunodeficient mice are generated by crossing an inbred strain of mouse expressing the human Stem Cell Factor SCF$^{220}$ transgene with NOD-scid, NSG or NRG mice.

Congenic strains of mice expressing human Stem Cell Factor SCF$^{220}$ are derived from hemizygous transgenic mice expressing human Stem Cell Factor SCF$^{220}$ described in Majumdar et al., Blood, 87 (8):3203, 1996. These mice on the C3H/HeJ strain background express human SCF$^{220}$ from a cassette including the human SCF$^{220}$ cDNA expressed from the human phosphoglycerate kinase (PGK) promoter. The PGK promoter includes a 514 bp 5'-flanking sequence from the X-linked human phosphoglycerate kinase-1 gene up to but excluding the translational start codon. The hSCF$^{220}$ cDNA in addition to a splice donor/acceptor and poly A site is adjoined to the 3' end the PGK promoter to generate the expression cassette. The hemizygous transgenic mice are bred with an inbred strain (recipient strain). Mice at a particular backcross generation (i.e. N10) are screened and homozygous congenic lines derived from strains that display crossover close to the gene of interest.

The resulting transgenic immunodeficient mice are designated NOD.Cg-Prkdc$^{scid}$ Il2rg$^{tm1Wjl}$Tg(PGK1-KITLG*220)441Daw/J, abbreviated as NOD scid gamma Tg)hu-mSCF$^{220}$ (NSG-Tg(humSCF$^{220}$) mice, and NOD.Cg-Rag1$^{tm1Mom}$Il2rg$^{tm1Wjl}$/SzJ Tg(PGK1-KITLG*220) Daw/J, abbreviated as NRG-Tg(humSCF$^{220}$) mice.

Generation of Transgenic HSC$^{248}$ Mice

Congenic strains of mice expressing human Stem Cell Factor SCF$^{248}$ are derived from heterozygous transgenic mice expressing human Stem Cell Factor SCF$^{248}$ described in Majumdar et al., Blood, 87 (8):3203, 1996. These mice express human SCF$^{248}$ from a cassette including the human SCF$^{248}$ cDNA expressed from the human phosphoglycerate kinase (PGK) promoter. The PGK promoter includes a 514 bp 5'-flanking sequence from the X-linked human phosphoglycerate kinase-1 gene up to but excluding the translational start codon. The hSCF$^{248}$ cDNA in addition to a splice donor/ acceptor and poly A site is adjoined to the 3' end the PGK promoter in to generate the expression cassette. The hemizygous transgenic mice are bred with an inbred strain (recipient strain). Mice at a particular backcross generation (i.e. N10) are screened and homozygous congenic lines derived from strains that display crossover close to the gene of interest.

The resulting transgenic immunodeficient mice are designated NOD.Cg-Prkdc$^{scid}$ Il2rg$^{tm1Wjl}$/SzJ Tg(PGK1-KITLG*248)441Daw/J abbreviated as NOD scid gamma Tg huSCF$^{248}$ (NSG-Tg(huSCF$^{248}$) mice, and NOD.Cg-Rag1$^{tm1Mom}$Il2rg$^{tm1Wjl}$/SzJ Tg(PGK1-KITLG*248) Daw/J, abbreviated as NRG-Tg(huSCF$^{248}$) mice.

Characterization of Transgenic Mice

Transgenic mice are tested for the presence of the transgene by analyzing tail DNA.

PCR is used to identify hu-mSCF$^{220}$ transgenics (both hu-mSCF$^{220}$/+ hemizygotes and hu-mSCF$^{220}$/hu-mSCF$^{220}$ homozygotes). Primers PGKtv-F and PGKtv-R are used to amplify a region of the huPGK-1 promoter included in the transgene. The sequences of these primers are:PGKtv-F:5'-aca ttc tta cgt ccg ttc gc-3' (SEQ ID No. 6) and PGKtv-R:5'-act agt gag acg tgc ggc tt-3' (SEQ ID No. 7). Each PCR reaction mixture contains 2 microliters DNA (50-100 ng), 2.5 microliters 10× Buffer, 2 microliters 2.5 mM dNTP's, 0.5 microliters, 20 uM primer: PGKtv-F, 0.5 microliters 20 μM primer: PGKtv-R, 0.1 microliter taq polymerase, 14.7 microliters dH$_2$O and 2.7 microliters Cresol Red. The PCR reaction conditions include: Initial Prime at 94° C. for 4'; Prime at 94° C. for 30"; Anneal at 60° C. for 30"; Extend at 72° C. for 1'; Extension Hold at 72° C. for 4' and Final hold at 10° C. until analysis. Thirty PCR cycles are performed.

A real time PCR reaction is used to discriminate the hemizygous transgenics from the homozygous transgenics. Primers HuSCF-F and HuSCF-R are used to amplify a 79 bp region of exon 2 of the HuSCF sequence included in the transgene. The sequences of these primers are: HuSCF F: 5'cca aaa gac tac atg ata acc ctc aa3' (SEQ ID No. 8) and HuSCF-R: 5'cca tct cct tat cca aca atg3' (SEQ ID No. 9). A second set of included primers amplifies a 73 bp region of the apolipoprotein B gene. The sequences of these primers are: ApoB-F:5'cac gtg ggc tcc agc att3' (SEQ ID No. 10) and ApoB-R:5'tca cca gtc att tct gcc ttt g'3 (SEQ ID No. 11). Each PCR reaction mixture contains 5.5 microliters dH$_2$0, 12.5 microliters 2× Universal Master Mix, 1 microliter 20 µM primer APO-B F, 1 microliter 20 µM primer APO-B R, 1 microliter 20 µM primer:HuSCF F, 1 microliter 20 µM primer:HuSCF R, 1 microliter 5 µM ApoB probe, 1 microliter 5 µM HuSCF220 probe and 1 microliter DNA (0.5 ng/µl). The PCR reaction conditions include: stage 1 at 50° C. for 2:00, stage 2 at 95° C. for 10:00 and 95° C. for 0:15 and stage 3 at 60° C. for 1:00. Forty PCR cycles are performed. Probes used to identify products include: ApoB VIC-cca atg gtc ggg cac tgc tca a-TAMRA (SEQ ID No. 12) and HuSCF-220 6FAM-ctt ggc aaa aca tcc atc ccg gg-TAMRA (SEQ ID No. 13).

HSC Engraftment in Transgenic Mice

Stem Cells

Hematopoietic stem cells for use in generating humanized mice can be obtained from several different tissues, including umbilical cord blood (UCB) such as described in Ito et al., 2002; Traggiai et al., 2004; Ishikawa et al., 2005, bone marrow such as described in Holyoake et al., 1999, G-CSF-mobilized peripheral blood, such as described in Shultz et al., 2005, and fetal liver such as described in Holyoake et al., 1999.

Hematopoietic stem cell engraftment of immunodeficient transgenic mice is generally performed as described in T. Pearson et al., Curr. Protoc. Immunol. 81:15.21.1-15.21.21, 2008 with the proviso that methods of the present invention provide xenogenic hematopoietic stem cell engraftment without irradiating the recipient animal. A number of different engraftment routes can be used including, without limitation, intrahepatic, intravenous via the facial vein, intravenous via the intracardiac route, and intraperitoneal injections.

In this example, engraftment of newborn mice with T cell-depleted UCB stem cells via intrahepatic and intracardiac injection routes is described.

The isolated T cell-depleted UCB stem cells are suspended in PBS at a concentration of 6×10$^5$ CD34$^+$ cells/ml.

For irradiation of mice, 24- to 48-hr post-natal pups from a single litter are placed into a 100-mm$^2$ petri dish along with a small amount of bedding material from the breeder cage. The pups are irradiated with 100 cGy whole body irradiation (WBI) by exposure to a $^{137}$Cs source or by alternate irradiation protocols.

Irradiated or non-irradiated pups are anesthetized by lowering body temperature using ice. Upon sufficient anesthesia, each pup is injected by intracardiac or intrahepatic injection with 3×10$^4$ CD34+ cells in a 50 microliter volume.

Flow Cytometry

The phenotypes of murine cells are determined as described in Shultz L D et al. J. Immunol. 2005; 174:6477-6489. Anti-human mAb antibodies are purchased as FITC, PE, APC, PerCP, AlexaFluor 700, Pacific Blue, and PECy7 conjugates in order to accommodate seven-color flow cytometric analysis in the combinations indicated in Table 2 and Supplementary Tables 1, 2 and 3. Commercially available antibodies against human hematopoietic, lymphoid, and myeloid cell markers anti-CD3, CD4, CD8, CD10, CD13, CD14, CD20, CD33, CD34, CD45, CD45RA, CD45RO, CD64, and CD71, anti-human FoxP3, anti-human CD123, anti-human BDCA2, anti-human CD11c and anti-human CD235a are used.

Single-cell suspensions of bone marrow, spleen, and thymus are prepared from non-engrafted and human HSC-engrafted mice. Whole blood is collected in heparin. Single cell suspensions of 1×10$^6$ cells in a 50 µL volume or 100 µL of whole blood are pre-incubated with rat anti-mouse FcR11b (clone 2.4G2) to block Fc binding. Cells are prepared for flow cytometry as described in Shultz L D et al. J. Immunol. 2005; 174:6477-6489; Pearson T et al. Clin. Exp. Immunol., 2008; 154:270-284; and Pearson T et al. Curr. Protoc. Immunol. 2008; Chapter 15:Unit. At least 50,000 events are acquired on BD Biosciences LSRII or FACSCalibur instruments (BD Biosciences). Data analysis is performed with FlowJo (Tree Star, Inc., Ashland, Oreg.) software.

Flow Cytometric Analysis

Flow cytometry is used to evaluate xenogenic stem cell engraftment in SCF transgenic mice in this example.

A sample of whole blood is collected from engrafted irradiated and engrafted non-irradiated mice to be tested, along with a whole blood sample from a non-engrafted mouse as a negative control. Aliquots of each sample are dispensed into separate containers and stained with anti-human and anti-mouse CD45 antibodies. The cells are then analyzed using standard flow cytometric technique. The extent of xenogenic stem cell engraftment is assessed by analysis of the proportion of total nucleated cells that are positive for an engraftment marker. The extent of human stem cell engraftment is assessed by analysis of the proportion of total nucleated cells that are positive for human CD45.

Engraftment in Transgenic and Control Mice

In this example, twenty-four to 72 hour old NSG mice are non-irradiated or irradiated with 100 cGy. Twenty-four to 72 hour old NRG mice are non-irradiated or irradiated with 400 cGy. Irradiated and non-irradiated mice are injected with CD3 T cell-depleted umbilical cord blood (UCB) containing 3×10$^4$ CD34+HSC in a 50 µL volume via intracardic injection. Engraftment of the human immune system is determined by flow cytometry 12 weeks later.

Flow Cytometric Analysis

Human membrane-bound SCF transgenic NSG mice [NSG-Tg(hu-mSCF)] are generated and bred to homozygosity as described. Bone marrow flow cytometric analyses are performed comparing non-engrafted NSG and NSG-Tg(hu-mSCF) mice. Differences are observed in the Gr1+Mac1+ population, but not in other populations examined as shown in Table I.

TABLE I

Flow summary table of 12 week old male mice; huSCF mice are homozygous for transgene - non-engrafted mice

| Bone Marrow Surface Marker | NOD +/+ (%) (N = 1) | NOD scid IL2rg (%) (N = 4) | NOD scid IL2rg Tg(hu-mSCF) (%) (N = 5) |
|---|---|---|---|
| CD3$^+$/CD4$^+$ | 0.6 | 0.0 ± 0.0 | 0.0 ± 0.0 |
| CD3$^+$/CD8$^+$ | 0.43 | 0.0 ± 0.0 | 0.0 ± 0.0 |
| B220$^+$/IgK, light chain$^+$ | 6.02 | 0.0 ± 0.0 | 0.0 ± 0.0 |
| B220$^+$/IgK, light chain$^-$ | 7.58 | 0.5 ± 0.0 | 0.5 ± 0.0 |
| GR-1$^+$/Mac-1$^+$ | 35.6 | 44.0 ± 0.7 | 38.3 ± 1.0** |
| GR-1$^-$/Mac-1$^+$ | 8.17 | 9.8 ± 0.2 | 10.7 ± 0.4 |
| Ter 119$^+$ | 30 | 32.9 ± 0.5 | 36.0 ± 1.6 |
| DX5$^+$/CD122$^+$ | 1.58 | 0.9 ± 0.0 | 1.3 ± 0.0 |
| LGL$^+$/CD122$^+$ | 0.0 | 0.0 ± 0.0 | 0.0 ± 0.0 |
| MHC I$^+$ | 94.3 | 92.7 ± 0.6 | 89.6 ± 0.6** |
| MHC I$^+$/MHC II$^+$ | 16.8 | 7.8 ± 0.2 | 8.3 ± 0.2 |

**<0.01

Engraftment of Adult NSG and NSG-Tg(hu-mSCF) Mice with Human HSC

Adult NSG and NSG-Tg(hu-mSCF) mice are non-irradiated and engrafted with 3×10$^4$ T cell-depleted CD34+ umbilical cord blood-derived HSC.

At 12 weeks of age, engraftment of human hematopoietic cells in transgenic and control mice is determined by flow cytometry. Non-irradiated adult NSG and NSG-Tg(hu-mSCF) mice consistently exhibit engraftment with human hematopoietic CD45+ cells in the spleen 12 weeks after injection with human HSC as shown in Table II. The number of human CD45+ cells in the spleen of NSG-Tg(hu-mSCF) mice is ~3-fold higher than that attained in NSG mice.

TABLE II

| Spleen | NOD-scid IL2rγc$^{null}$hu-mSCF No rad (N = 6) | NOD-scid IL2rγc$^{null}$ No rad (N = 6) |
|---|---|---|
| Total spleen cells (×10$^6$) | 18.7 ± 13 | 5.1 ± 2.6 |
| Percent Human Leukocytes | | |
| CD45+ | 65.9 ± 30 | 74.4 ± 11 |
| Percent of Human CD45+ | | |
| B Lineage | | |
| CD20+ | 53.0 ± 9.1 | 54.8 ± 11 |
| Myeloid/Granulocytic | | |
| CD33+ | 5.30 ± 4.2 | 1.95 ± 1.1 |
| T Linkage | | |
| CD3+ | 0.22 ± 0.39 | .015 ± 0.20 |
| Dendritic Subsets | | |
| CD11c+ | 1.26 ± 1.1 | 0.49 ± 0.16 |
| CD123+ | .57 ± 2.1 | 1.71 ± 0.60 |
| Monocyte/Macrophage | | |
| CD14+ | 0.16 ± 0.19 | 0.13 ± 0.03 |

Non-irradiated adult NSG and NSG-Tg(hu-mSCF) mice consistently exhibit engraftment with human hematopoietic CD45+ cells in the blood 12 weeks after injection with human HSC as shown in Table III, flow cytometric analysis of human cell content and leukocyte subpopulations in the peripheral blood of adult-engrafted mice.

TABLE III

| BLOOD | NOD-scid IL2rγc$^{null}$hu-mSCF no rad (N = 6) | NOD-scid IL2rγc$^{null}$ No rad (N = 6) |
|---|---|---|
| Percent Human Leukocytes | | |
| CD45+ | 38.3 ± 17 | 40.8 ± 12 |
| Percent Human CD45 | | |
| B Lineage | | |
| CD20+ | 81.3 ± 11 | 71.2 ± 7.9 |
| Myeloid/Granulocytic | | |
| CD33+ | 0.96 ± 0.66 | 0.70 ± 0.29 |
| T Lineage | | |
| CD3+ | 0.49 ± 0.94 | 0.57 ± 0.73 |
| Dendritic Subsets | | |
| CD11c+ | 5.06 ± 3.1 | 2.72 ± 1.0 |
| CD123+ | 0.34 ± 0.20 | 0.66 ± 0.70 |
| Monocyte/Macrophage | | |
| CD14+ | 0.64 ± 0.50 | 0.37 ± 0.26 |

Non-irradiated adult NSG and NSG-Tg(hu-mSCF) mice consistently exhibit engraftment with human hematopoietic CD45+ cells in the bone marrow 12 weeks after injection with human HSC as shown in Table IV.

TABLE IV

| Bone Marrow | NOD-Scid IL2rγc$^{null}$hu-mSCF No rad (N = 6) | NOD-Scid IL2rγc$^{null}$ No rad (N = 6) |
|---|---|---|
| Total bone marrow cells (×10$^6$) | 31.1 ± 9.6 | 33.1 ± 7.9 |
| Percent Human Leukocytes | | |
| CD45 | 76.6 ± 12 | 60.2 ± 17 |
| Percent of Human CD45+ | | |
| Myeloid/Granulocytic | | |
| CD33+ | 0.00 ± 0.0 | 0.00 ± 0.0 |
| Hematopoietic Progenitor | | |
| CD34+38− | 0.28 ± 0.26 | 1.14 ± 2.5 |
| (Common) CD34 + 38+ | 16.1 ± 3.0 | 13.4 ± 2.9 |
| Erythroblast/RBC | | |
| CD71+ (of CD45−) | 2.40 ± 1.6 | 3.50 ± 3.7 |
| CD71+235a+ | 36.3 ± 16 | 1.22 ± 1.27 |
| CD235a+ | 0.29 ± 0.29 | 0.07 ± 0.08 |
| Dendritic Subsets | | |
| CD11c+ | 0..01 ± 0.00 | 0.02 ± 0.03 |
| CD123+ | 0.04 ± 0.04 | 0.01 ± 0.01 |
| Monocyte/Macrophage | | |
| CD14+ | 0.01 ± 0.01 | 0.00 ± 0.00 |

In both unirradiated HSC-engrafted NSG and NSG-Tg(hu-mSCF) mice, normal ratios of developing human thymocyte subsets (CD4+CD8+, CD4+CD8−, and CD4−CD8+) cells are observed as shown in Table V.

TABLE V

| THYMUS | NOD-scid IL2rγc$^{null}$hu-mSCF no rad (N = 6) | NQD-scid IL2rγc$^{null}$ No rad (N = 6) |
|---|---|---|
| Percent Human Leukocytes | | |
| CD45 | 15.4 ± 19 | 20.0 ± 27 |
| Developing T Subsets | | |
| CD4+CD8+ | 58.6 ± 44 | 60.7 ± 34.3 |
| CD4+ | 2.09 ± 2.0 | 6.62 ± 5.7 |
| CD8+ | 4.84 ± 4.2 | 6.9 ± 4.4 |

Human Cell Development in the Blood of Newborn Human HSC-Engrafted NSG and NSG-Tg(hu-mSCF) Mice Four groups of newborn mice are engrafted with human HSC: 1) unirradiated NSG; 2) 100 cGy irradiated NSG mice; 3) unirradiated NSG-Tg(hu-mSCF) mice; and 4) 100 cGy irradiated NSG-Tg(hu-mSCF).

Figure 1B:
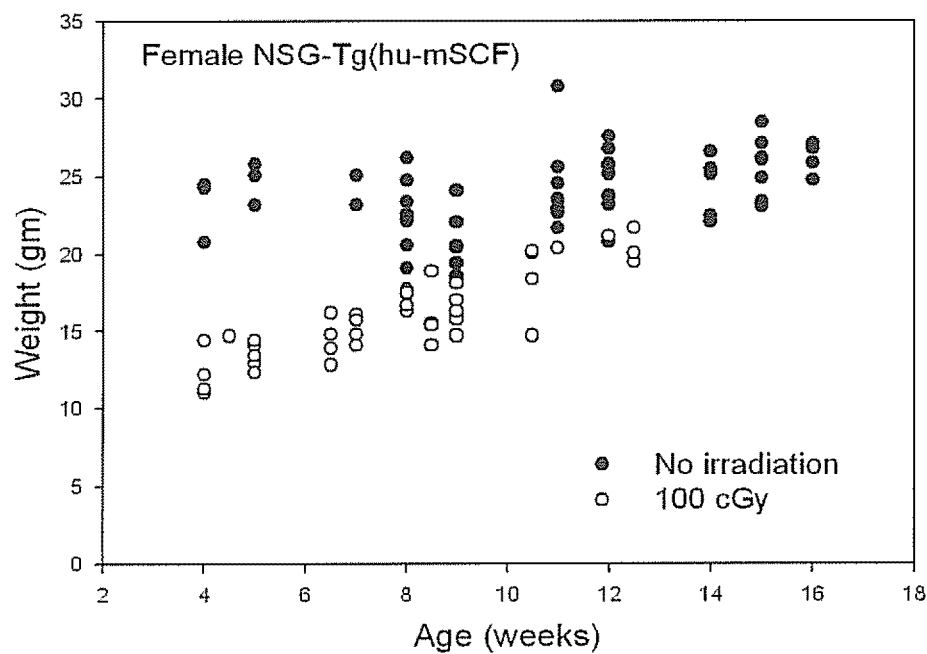
FIG. 1B is a graph showing the weights of unirradiated and 100 cGy irradiated NSG-Tg(hu-mSCF) male mice with age.

The unirradiated NSG-Tg(hu-mSCF) mice gain weight with much faster kinetics and attain higher adult weights than do irradiated NSG-Tg(hu-mSCF) as shown in FIGS. 1A and 1B.

Figure 2A:
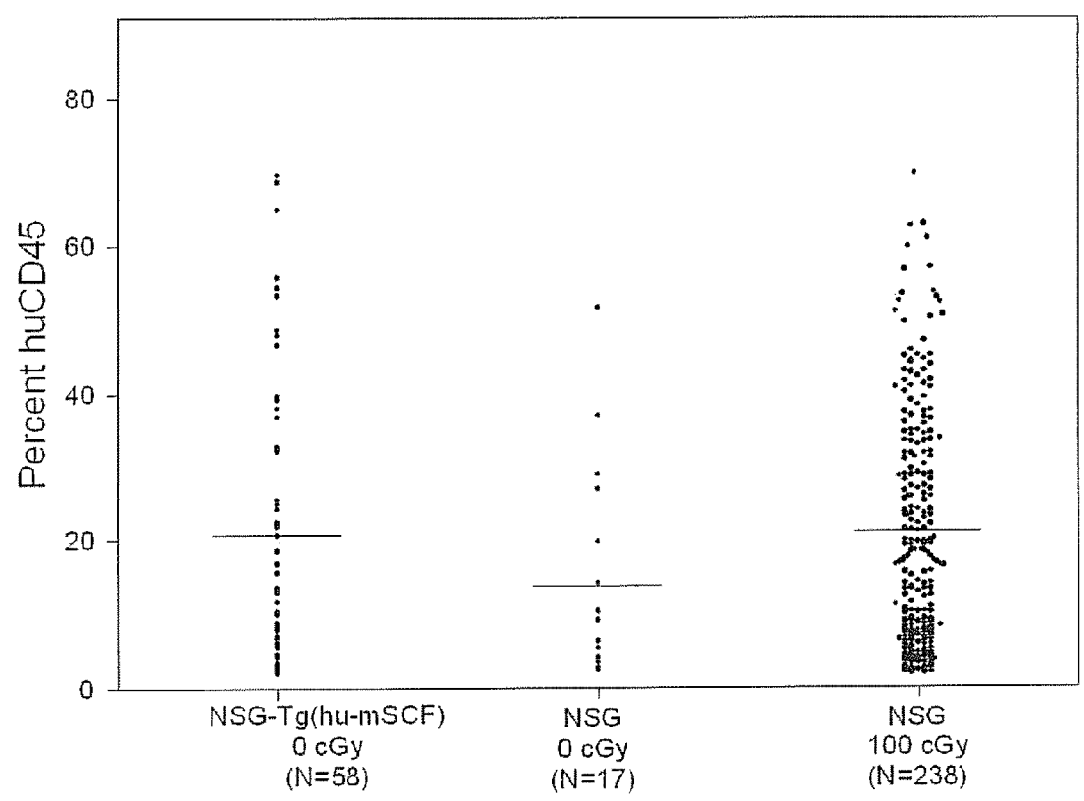
FIG. 2A is a graph showing the percent of human CD45+ cells in the blood of unirradiated NSG, unirradiated NSG-Tg (hu-mSCF), and 100 cGy NSG mice engrafted with human HSC as newborns and analyzed by flow cytometry at 12 weeks of age.
Figure 2B:
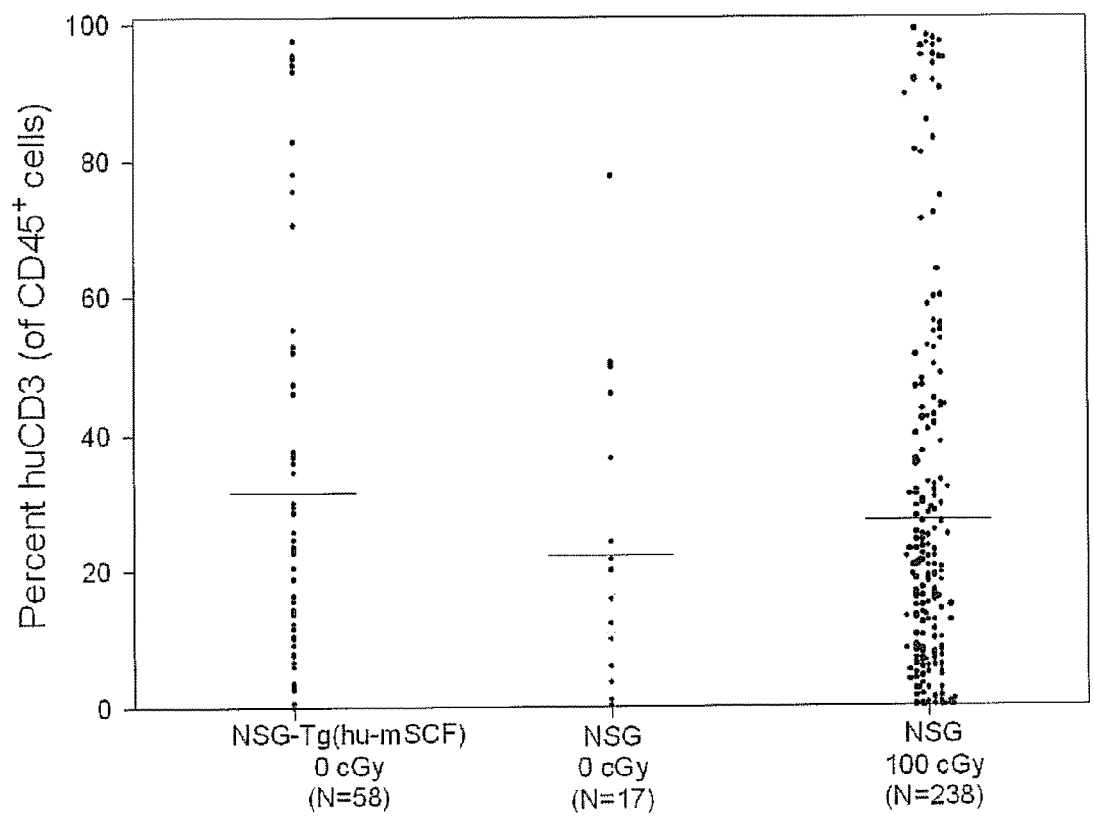
FIG. 2B is a graph showing the percent of human CD3+ cells in the blood of unirradiated NSG, unirradiated NSG-Tg (hu-mSCF), and 100 cGy NSG mice engrafted with human HSC as newborns and analyzed by flow cytometry at 12 weeks of age.

The frequency of engrafted mice, where "engrafted mice" is defined as >2% human CD45+ cells in the blood, is equivalent between unirradiated NSG (74%), irradiated NSG (83%) and unirradiated NSG-Tg(hu-mSCF) (70%) mice. FIGS. 2A and 2B show unirradiated NSG, unirradiated NSG-Tg(hu-mSCF), and 100 cGy NSG newborn mice are engrafted with human HSC and analyzed by flow cytometry for the percent of human CD45+ and CD3+ cells in the blood at 12 weeks of age. No significant difference between groups is observed.

The percent human CD45+ and CD3+ cells engrafted in the blood of each group is also equivalent as shown in FIGS. 2A and 2B, percent engraftment of human CD45+ and CD3+ cells in the blood of newborn engrafted mice at 12 weeks of age.

The absolute number of human CD45+ cells in the bone marrow of 100 cGy irradiated NSG mice and unirradiated NSG-Tg(hu-mSCF) are similar (p=n.s.) and both are significantly increased as compared to the absolute number of unirradiated NSG mice (p<0.01). As in blood, there are no significant differences in the percent of human CD45+ cell subsets. There is a significant increase in the percent of CD71+CD45− erythroid precursors as well as increased CD71+235a+ erythroid progenitor cells in unirradiated NSG-Tg(hu-mSCF) as compared to unirradiated NSG mice as shown in Table VI.

TABLE VI

Figure 3A:
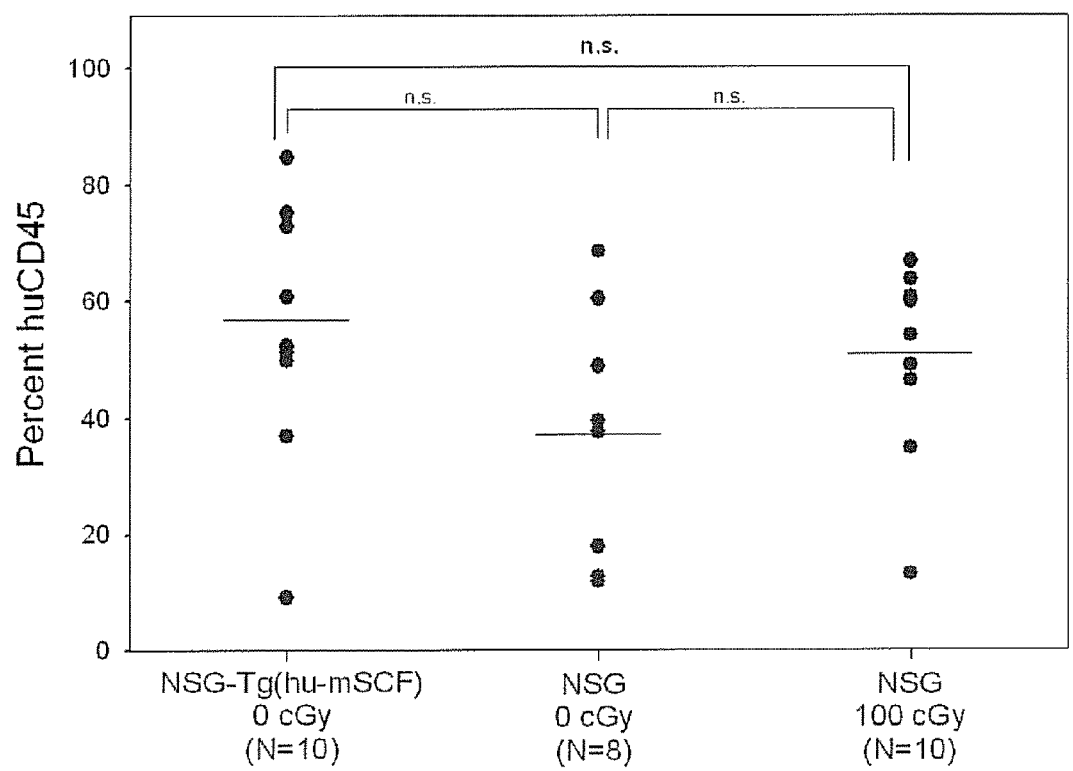
FIG. 3A is a graph showing the percent of human CD45+ cells in the blood of a matched cohort of unirradiated NSG, unirradiated NSG-Tg(hu-mSCF), and 100 cGy NSG mice engrafted with human HSC as newborns and analyzed by flow cytometry at 12 weeks of age.
Figure 3B:
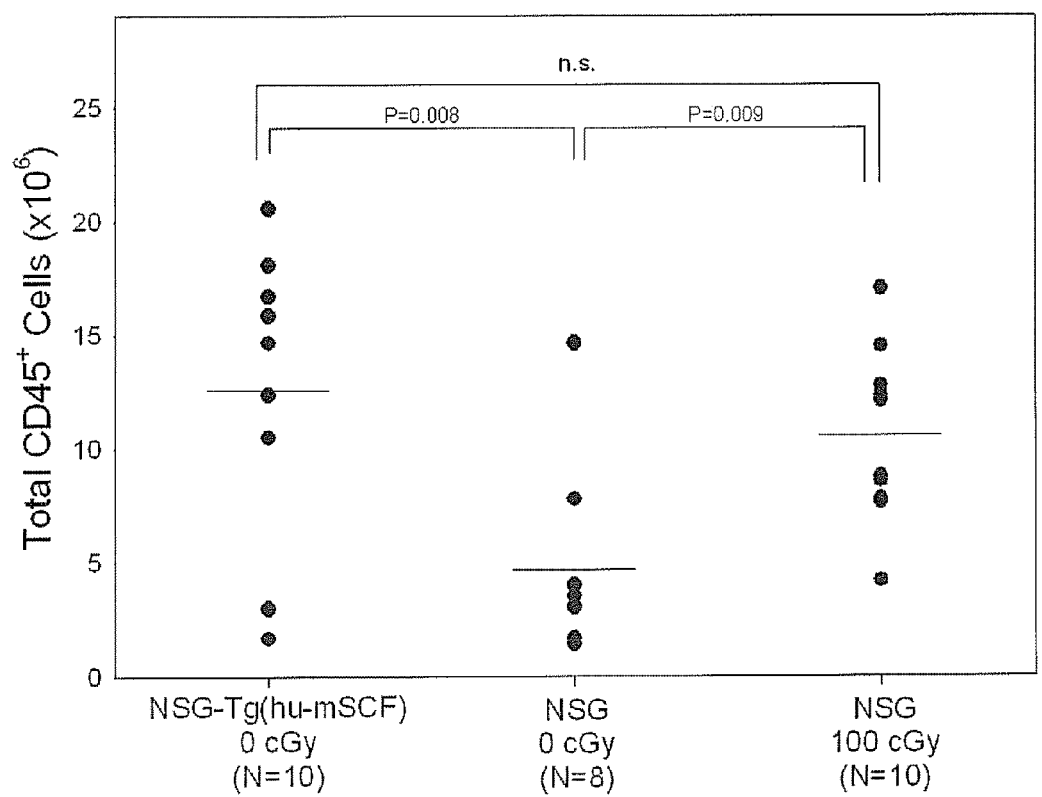
FIG. 3B is a graph showing the number of human CD45+ cells in the blood of unirradiated NSG, unirradiated NSG-Tg (hu-mSCF), and 100 cGy NSG mice engrafted with human HSC as newborns and analyzed by flow cytometry at 12 weeks of age.

| Bone Marrow | NOD-Scid IL2rγc$^{null}$huSCF no rad (N = 10) | NOD-Scid IL2rγc$^{null}$huSCF 100 rad (N = 7) | NOD-Scid IL2rγc$^{null}$ no rad (N = 8) | NOD-Scid IL2rγc$^{null}$ 100 rad (N = 10) |
|---|---|---|---|---|
| Total bone marrow cells (×10$^6$) | 20.4 ± 8.4 | 7.6 ± 5.9 | 11.4 ± 4.7 | 18.7 ± 5.7 |
| Percent Human Leukocytes | | | | |
| CD45 | 63.0 ± 24 | 79.5 ± 10 | 39.7 ± 21 | 65.0 ± 18.4 |
| Percent of Human CD45+ | | | | |
| B Lineage | | | | |
| CD20+ | 4.04 ± 1.7 | 2.58 ± 1.4 | 6.75 ± 3.9 | 3.92 ± 2.2 |
| CD10+20+ | 9.89 ± 5.1 | 9.32 ± 6.4 | 18.6 ± 6.8 | 8.54 ± 4.4 |
| CD10+ | 51.2 ± 21 | 53.1 ± 26.6 | 59.5 ± 12 | 57.2 ± 24.6 |
| Myeloid/Granulocytic | | | | |
| CD33+ | 4.21 ± 3.3 | 9.41 ± 8.1 | 4.86 ± 2.9 | 6.71 ± 3.8 |
| CD33+64+ | 5.10 ± 4.8 | 6.56 ± 7.0 | 0.76 ± 0.61 | 6.07 ± 7.5 |
| CD64+ | 1.81 ± 1.2 | 0.49 ± 0.61 | 0.72 ± 0.11 | 1.45 ± 1.59 |
| Hematopoietic Progenitor | | | | |
| CD34+38− (Common) | 0.27 ± 0.3 | 0.43 ± 0.35 | 0.03 ± 0.03 | 0.63 ± 0.46 |
| CD34+38+ | 3.85 ± 2.6 | 5.47 ± 2.3 | 6.50 ± 3.3 | 6.4 ± 3.9 |
| Erythroblast/RBC | | | | |
| Percent of Human CD45− | | | | |
| CD71+ (of CD45−) | 2.17 ± 2.8 | 1.62 ± 1.0 | 0.22 ± 0.18 | 0.55 ± 0.60 |
| CD71+235a+ | 4.65 ± 5.7 | 25.49 ± 22 | 0.13 ± 0.26 | 0.60 ± 0.60 |
| CD235a+ | 0.47 ± 0.6 | 3.30 ± 3.2 | 0.05 ± 0.02 | 0.27 ± 0.31 |
| Percent of Human CD45+ | | | | |
| Dendritic Subsets | | | | |
| CD11c+ | 0.93 ± 0.71 | 1.00 ± 0.78 | 0.58 ± 0.33 | 1.51 ± 1.67 |
| CD123+ | 2.08 ± 1.9 | 2.46 ± 1.9 | 3.70 ± 2.26 | 1.92 ± 1.43 |
| BDCA2+ | 0.16 ± 0.15 | 0.03 ± 0.01 | 0.06 ± 0.03 | 0.13 ± 0.16 |
| BDCA2+/123+ | 1.89 ± 1.9 | 1.98 ± 1.7 | 2.40 ± 1.58 | 1.76 ± 1.43 |
| Monocyte/Macrophage | | | | |
| CD14+ | 6.23 ± 5.7 | 7.13 ± 6.5 | 2.79 ± 1.7 | 7.32 ± 6.4 |
| CD14+/CD16+ | 0.00 ± 0.00 | 0.170.17 | 0.09 ± 0.07 | 0.05 ± 0.05 |
| CD16+ | 0.04 ± 0.05 | 0.15 ± 0.13 | 0.26 ± 0.10 | 0.07 ± 0.08 |
| NK Cell | | | | | human CD45+ cells that are present in unirradiated NSG mice (p<0.01) as shown in FIGS. 3A and 3B.

FIGS. 3A and 3B show unirradiated NSG, unirradiated NSG-Tg(hu-mSCF), and 100 cGy NSG newborn mice are engrafted with human HSC analyzed by flow cytometry for the percent and number of human CD45+ and CD3+ cells in the bone marrow at 12 weeks of age. Significant differences between groups are noted in the figures.

Table VI shows flow cytometric analysis of human cell content and leukocyte subpopulations in the bone marrow of engrafted mice at 12 weeks of age. The absolute number of human CD45+ cells in the bone marrow of 100 cGy irradiated NSG mice and unirradiated NSG-Tg(hu-mSCF) are similar (p=n.s.) and both are significantly increased as compared to the absolute number of human CD45+ cells that are present in Human Cell Development in the Spleen of Newborn Human HSC-Engrafted NSG and NSG-Tg(hu-mSCF) Mice The percent of human CD45+ cells in the spleens of unirradiated NSG, irradiated NSG, and unirradiated NSG-Tg(hu-mSCF) mice engrafted with human HSC as newborns is similar at 12 weeks of age, but the absolute number of human CD45+ cells in the spleen of unirradiated NSG-Tg(hu-mSCF) mice is approximately 2.5-fold higher than that observed in unirradiated NSGT mice.

Table VII shows flow cytometric analysis of human cell content and leukocyte subpopulations in the spleen of engrafted nod-scid Il2rγ$^{null}$ hu-mSCF mice at 12 weeks of age.

TABLE VII

| Spleen | NOD-Scid IL2rγc$^{null}$huSCF no rad (N = 10) | NOD-Scid IL2rγc$^{null}$hu-mSCF 100 rad (N = 7) | NOD-Scid IL2rγc$^{null}$ no rad (N = 8) | NOD-Scid IL2rγc$^{null}$ 100 rad (N = 10) |
|---|---|---|---|---|
| Total spleen cells (×10$^6$) | 28.0 ± 16 | 12.2 ± 10 | 10.2 ± 7.0 | 16.5 ± 14 |
| Percent Human Leukocytes | | | | |
| CD45+ | 70.0 ± 9.2 | 62.8 ± 17 | 61.2 ± 19 | 66.9 ± 11 |
| Percent of Human CD45+ | | | | |
| B Lineage | | | | |
| CD20+ | 34.4 ± 19 | 31.1 ± 21 | 45.6 ± 16 | 42.5 ± 13 |
| CD20+/CD10+ | 15.0 ± 8.9 | 12.1 ± 13 | 23.7 ± 12 | 16.6 ± 7.9 |
| CD10+ | 7.07 ± 14 | 2.61 ± 3.6 | 12.1 ± 6.6 | 13.7 ± 21 |
| Myeloid/Granulocytic | | | | |
| CD33+ | 8.33 ± 13 | 12.3 ± 22 | 10.6 ± 0.41 | 1.45 ± 1.4 |
| CD33+64+ | 0.17 ± 0.54 | 0.33 ± 0.8 | 0.0 ± 0.0 | 0.00 ± 0.0 |
| CD64+ | 1.20 ± 3.1 | 1.47 ± 3.5 | 0.0 ± 0.0 | 0.31 ± 0.97 |
| T Lineage | | | | |
| CD3+ | 24.7 ± 18 | 29.45 ± 14.3 | 19.1 ± 12 | 20.8 ± 16 |
| CD4+ | 18.0 ± 14.4 | 16.8 ± 8.1 | 10.6 ± 8.0 | 12.8 ± 9.4 |
| CD4 RA:RO | 1.61 ± 3.5 | 0.17 ± 0.25 | 1.59 ± 0.94 | 0.41 ± 0.38 |
| CD8+ | 14.3 ± 16 | 11.2 ± 6.5 | 7.17 ± 4.4 | 7.47 ± 3.32 |
| CD8 RA:RO | 1.52 ± 2.0 | 0.88 ± 0.8 | 4.51 ± 1.8 | 3.36 ± 3.56 |
| Dendritic Subsets | | | | |
| CD11c+ | 0.08 ± 0.08 | 0.13 ± 0.06 | 2.02 ± 2.58 | 0.18 ± 0.20 |
| CD123+ | 0.20 ± 0.20 | 0.28 ± 0.17 | 0.25 ± 0.19 | 0.26 ± 0.27 |
| BDCA2+ | 0.01 ± 0.01 | 0.00 ± 0.00 | 0.02 ± 0.01 | 0.16 ± 0.15 |
| BDCA2+/123+ | 0.15 ± 0.17 | 0.12 ± 0.15 | 0.23 ± 0.20 | 1.57 ± 0.70 |
| Monocyte/Macrophage | | | | |
| CD14+ | 1.11 ± 1.1 | 1.10 ± 0.90 | 0.21 ± 0.15 | 1.06 ± 0.82 |
| CD14+/CD16+ | 0.21 ± 0.65 | 0.22 ± 0.21 | 0.03 ± 0.03 | 0.37 ± 0.95 |
| CD16+ | 0.05 ± 0.08 | 0.58 ± 0.73 | 0.24 ± 0.09 | 0.24 ± 0.09 |

Human Cell Development in the Thymus of Newborn Human HSC-Engrafted NSG and NSG-Tg(hu-mSCF) Mice In all four groups of mice, normal ratios of developing human thymocyte subsets (CD4+CD8+, CD4+CD8−, and CD4−CD8+) cells are observed as shown by flow cytometric analysis of human cell content and T subset development in the thymus of newborn engrafted NOD-scid IL2rγ$^{null}$ huSCF mice at 12 weeks of age, Table VIII.

TABLE VIII

| THYMUS | NOD-scid IL2rγc$^{null}$hu-, SCF no rad (N = 10) | NOD-scid IL2rγc$^{null}$hu-mSCF 100 rad (N = 7) | NOD-scid IL2rγc$^{null}$ no rad (N = 8) | NOD-scid IL2rγc$^{null}$ 100 rad (N = 10) |
|---|---|---|---|---|
| Total Human Leukocytes | | | | |
| CD45 | 46.2 ± 34 | 49.8 ± 31 | 62.6 ± 25 | 43.1 ± 33 |
| Developing T Subsets | | | | |
| CD4+CD8+ | 64.5 ± 16 | 34.1 ± 31.0 | 28.9 ± 29 | 50.3 ± 34 |
| CD4+ | 15.3 ± 10 | 22.9 ± 27 | 45.4 ± 28 | 22.4 ± 16 |
| CD8+ | 9.1 ± 4.0 | 13.2 ± 11 | 16.0 ± 8.2 | 13.6 ± 13 |

Figure 4:
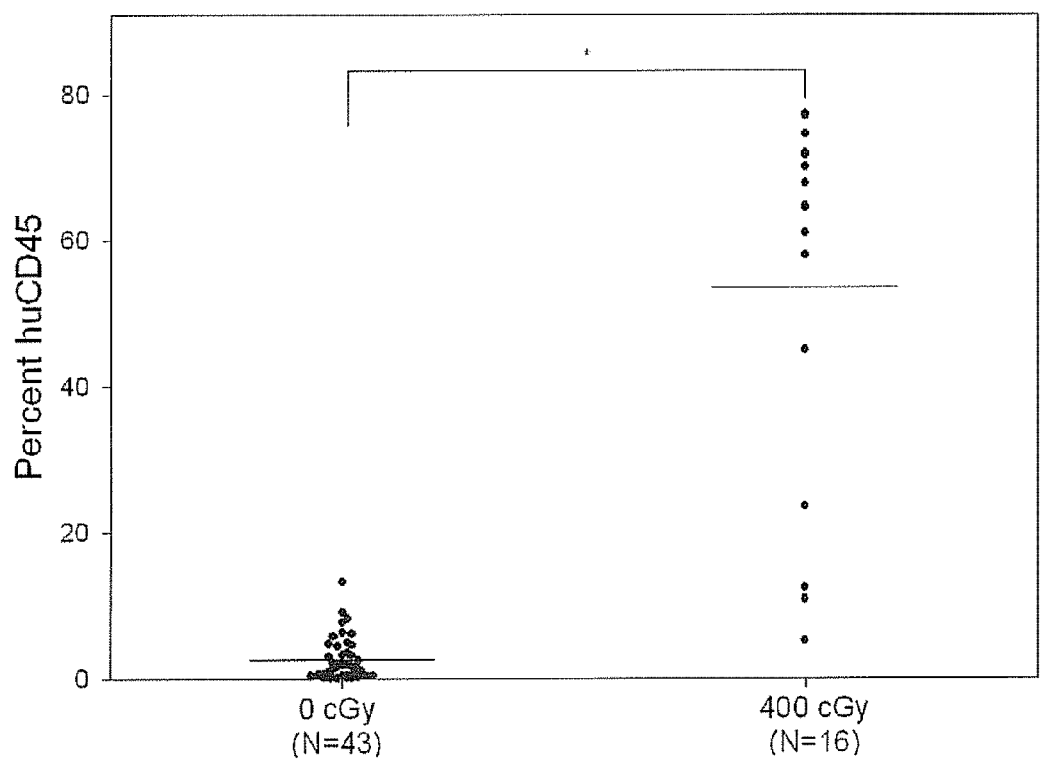
FIG. 4 is a graph showing the percent of human CD45+ cells in the blood of unirradiated NRG-Tg(hu-mSCF), and 400 cGy NRG newborn mice were engrafted with human HSC as newborns and analyzed by flow cytometry for the percent and number of human CD45+ cells in the blood at 12 weeks of age.

Poor Human Cell Engraftment in unirradiated Human HSC-Engrafted Newborn NOD-Rag1$^{null}$ IL2rγ$^{null}$ (NRG)-Tg(hu-mSCF) Mice To determine whether the engraftment of human HSC in unirradiated newborn NSG-Tg(hu-mSCF) mice is a characteristic of the NOD strain background or dependent on the scid mutation, NOD-Rag1$^{null}$ IL2rγ$^{null}$ (NRG)-Tg(hu-mSCF) mice are generated and engrafted unirradiated newborns with human HSC. As shown in FIG. 4, unirradiated newborn NRG-Tg(hu-mSCF) mice engrafted with human HSC exhibit poor human CD45+ cell engraftment at 12 weeks of age in their blood, bone marrow and spleen. In contrast, 400 cGy irradiated NRG mice engrafted with the same cord blood-derived human HSC generate high levels of human CD45+ cells at 12 weeks of age in all tissues examined as shown in FIG. 4, engraftment of human CD45 cells in the blood of newborn engrafted mice at 12 weeks of age. FIG. 4: Unirradiated NRG-Tg(hu-mSCF), and 400 cGy NRG newborn mice are engrafted with human HSC as described in Methods and analyzed by flow cytometry for the percent and number of human CD45+ cells in the blood at 12 weeks of age. Significant differences between groups are noted in the figure.

Skin Transplantation Protocol

HSC and non-HSC engrafted transgenic and control mice treated with anti-Gr-1 monoclocal antibody are transplanted with human split thickness skin grafts as described in Racki, W. J, et al. Transplantation 89, 527-536. 2010. Two irradiated NSG-Tg(hu-mSCF220) mice engrafted with HSC are examined at 5 weeks after skin graft and show complete rejection of the skin grafts, showing that the engrafted human immune system is functional. Seven unirradiated NSG-Tg(hu-mSCF220) mice engrafted with HSC are examined at 4 weeks after skin graft and all seven show some stage of rejection of the skin graft with two showing complete rejection of the skin grafts, indicating that the engrafted human immune system is functional in all of the HSC engrafted unirradiated mice.

Statistical Analyses

Most data is presented as the mean±one standard deviation. The flow cytometry data on human engraftment is presented as mean±standard error. Parametric data are compared by one-way ANOVA with Bonferroni post-tests to compare individual pair-wise groupings and nonparametric data are compared by a Kruskal-Wallis test with Dunns post-test to compare individual pair-wise groupings. Significant differences are assumed for p values<0.05. All statistical analyses are performed using GraphPad Prism software (version 4.0c, GraphPad, San Diego, Calif.).

Sequences

The amino acid sequences of SCF$^{220}$ $^{and}$ SCF$^{248}$ are shown along with exemplary nucleic acid sequences encoding the proteins.

SEQ ID NO. 1: Human SCF 220 (245 aa)

MKKTQTWILTCIYLQLLLFNPLVKTEGICRNRVTNNVKDVTKLVANL

PKDYMITLKYVPGMDVLPSHCWISEMVVQLSDSLTDLLDKFSNISEG

LSNYSIIDKLVNIVDDLVECVKENSSKDLKKSFKSPEPRLFTPEEFF

RIFNRSIDAFKDFVVASETSDCVVSSTLSPEKGKAKNPPGDSSLHWA

AMALPALFSLIIGFAFGALYWKKRQPSLTRAVENIQINEEDNEISML

QEKEREFQEV

SEQ ID NO. 2: Nucleotide Sequence Encoding Human SCF 220

ATGAAGAAGACACAAACTTGGATTCTCACTTGCATTTATCTTCAGCT

GCTCCTATTTAATCCTCTCGTCAAAACTGAAGGGATCTGCAGGAATC

GTGTGACTAATAATGTAAAAGACGTCACTAAATTGGTGGCAAATCTT

CCAAAAGACTACATGATAACCCTCAAATATGTCCCCGGGATGGATGT

TTTGCCAAGTCATTGTTGGATAAGCGAGATGGTAGTACAATTGTCAG

ACAGCTTGACTGATCTTCTGGACAAGTTTTCAAATATTTCTGAAGGC

TTGAGTAATTATTCCATCATAGACAAACTTGTGAATATAGTGGATGA

CCTTGTGGAGTGCGTGAAAGAAAACTCATCTAAGGATCTAAAAAAT

CATTCAAGAGCCCAGAACCCAGGCTCTTTACTCCTGAAGAATTCTTT

AGAATTTTTAATAGATCCATTGATGCCTTCAAGGACTTTGTAGTGGC

ATCTGAAACTAGTGATTGTGTGGTTTCTTCAACATTAAGTCCTGAGA

AAGGGAAGGCCAAAAATCCCCCTGGAGACTCCAGCCTACACTGGGCA

GCCATGGCATTGCCAGCATTGTTTTCTCTTATAATTGGCTTTGCTTT

TGGAGCCTTATACTGGAAGAAGAGACAGCCAAGTCTTACAAGGGCAG

TTGAAAATATACAAATTAATGAAGAGGATAATGAGATAAGTATGTTG

CAAGAGAAAGAGAGAGAGTTTCAAGAAGTGTAA

SEQ ID NO. 3: Human SCF 248 (273 aa)

MKKTQTWILTCIYLQLLLFNPLVKTEGICRNRVTNNVKDVTKLVANL

PKDYMITLKYVPGMDVLPSHCWISEMVVQLSDSLTDLLDKFSNISEG

LSNYSIIDKLVNIVDDLVECVKENSSKDLKKSFKSPEPRLFTPEEFF

RIFNRSIDAFKDFVVASETSDCVVSSTLSPEKDSRVSVTKPFMLPPV

AASSLRNDSSSSNRKAKNPPGDSSLHWAAMALPALFSLIIGFAFGAL

YWKKRQPSLTRAVENIQINEEDNEISMLQEKEREFQEV

SEQ ID NO. 4 Coding Sequence for Human SCF 248

ATGAAGAAGACACAAACTTGGATTCTCACTTGCATTTATCTTCAGCT

GCTCCTATTTAATCCTCTCGTCAAAACTGAAGGGATCTGCAGGAATC

GTGTGACTAATAATGTAAAAGACGTCACTAAATTGGTGGCAAATCTT

CCAAAAGACTACATGATAACCCTCAAATATGTCCCCGGGATGGATGT

TTTGCCAAGTCATTGTTGGATAAGCGAGATGGTAGTACAATTGTCAG

ACAGCTTGACTGATCTTCTGGACAAGTTTTCAAATATTTCTGAAGGC

TTGAGTAATTATTCCATCATAGACAAACTTGTGAATATAGTGGATGA

CCTTGTGGAGTGCGTGAAAGAAAACTCATCTAAGGATCTAAAAAAT

CATTCAAGAGCCCAGAACCCAGGCTCTTTACTCCTGAAGAATTCTTT

AGAATTTTTAATAGATCCATTGATGCCTTCAAGGACTTTGTAGTGGC

ATCTGAAACTAGTGATTGTGTGGTTTCTTCAACATTAAGTCCTGAGA

AAGATTCCAGAGTCAGTGTCACAAAACCATTTATGTTACCCCCTGTT

GCAGCCAGCTCCCTTAGGAATGACAGCAGTAGCAGTAATAGGAAGGC

CAAAAATCCCCCTGGAGACTCCAGCCTACACTGGGCAGCCATGGCAT

TGCCAGCATTGTTTTCTCTTATAATTGGCTTTGCTTTTGGAGCCTTA

TACTGGAAGAAGAGACAGCCAAGTCTTACAAGGGCAGTTGAAAATAT

ACAAATTAATGAAGAGGATAATGAGATAAGTATGTTGCAAGAGAAAG

AGAGAGAGTTTCAAGAAGTGTAA

SEQ ID NO. 5 Nucleotide Sequence Encoding Human SCF 248 Including 5' and 3' Non-Coding Sequences

CCGCCTCGCGCCGAGACTAGAAGCGCTGCGGGAAGCAGGGACAGTGG

AGAGGGCGCTGCGCTCGGGCTACCCAATGCGTGGACTATCTGCCGCC

GCTGTTCGTGCAATATGCTGGAGCTCCAGAACAGCTAAACGGAGTCG

CCACACCACTGTTTGTGCTGGATCGCAGCGCTGCCTTTCCTTATGAA

GAAGACACAAACTTGGATTCTCACTTGCATTTATCTTCAGCTGCTCC

-continued

```
TATTTAATCCTCTCGTCAAAACTGAAGGGATCTGCAGGAATCGTGTG

ACTAATAATGTAAAAGACGTCACTAAATTGGTGGCAAATCTTCCAAA

AGACTACATGATAACCCTCAAATATGTCCCCGGGATGGATGTTTTGC

CAAGTCATTGTTGGATAAGCGAGATGGTAGTACAATTGTCAGACAGC

TTGACTGATCTTCTGGACAAGTTTTCAAATATTTCTGAAGGCTTGAG

TAATTATTCCATCATAGACAAACTTGTGAATATAGTGGATGACCTTG

TGGAGTGCGTGAAAGAAAACTCATCTAAGGATCTAAAAAAATCATTC

AAGAGCCCAGAACCCAGGCTCTTTACTCCTGAAGAATTCTTTAGAAT

TTTTAATAGATCCATTGATGCCTTCAAGGACTTTGTAGTGGCATCTG

AAACTAGTGATTGTGTGGTTTCTTCAACATTAAGTCCTGAGAAAGAT

TCCAGAGTCAGTGTCACAAAACCATTTATGTTACCCCCTGTTGCAGC

CAGCTCCCTTAGGAATGACAGCAGTAGCAGTAATAGGAAGGCCAAAA

ATCCCCCTGGAGACTCCAGCCTACACTGGGCAGCCATGGCATTGCCA

GCATTGTTTTCTCTTATAATTGGCTTTGCTTTTGGAGCCTTATACTG

GAAGAAGAGACAGCCAAGTCTTACAAGGGCAGTTGAAAATATACAAA

TTAATGAAGAGGATAATGAGATAAGTATGTTGCAAGAGAAAGAGAGA

GAGTTTCAAGAAGTGTAAATTGTGGCTTGTATCAACACTGTTACTTT

CGTACATTGGCTGGTAACAGTTCATGTTTGCTTCATAAATGAAGCAG

CTTTAAACAAATTCATATTCTGTCTGGAGTGACAGACCACATCTTTA

TCTGTTCTTGCTACCCATGACTTTATATGGATGATTCAGAAATTGGA

ACAGAATGTTTTACTGTGAAACTGGCACTGAATTAATCATCTATAAA

GAAGAACTTGCATGGAGCAGGACTCTATTTTAAGGACTGCGGGACTT

GGGTCTCATTTAGAACTTGCAGCTGATGTTGGAAGAGAAAGCACGTG

TCTCAGACTGCATGTACCATTTGCATGGCTCCAGAAATGTCTAAATG

CTGAAAAAACACCTAGCTTTATTCTTCAGATACAAACTGCAG
```

SEQ ID NO. 14: Human Soluble SCF (164 aa and 25 aa N-Terminal Signal Peptide)

```
MKKTQTWILTCIYLQLLLFNPLVKTEGICRNRVTNNVKDVTKLVANL

PKDYMITLKYVPGMDVLPSHCWISEMVVQLSDSLTDLLDKFSNISEG

LSNYSIIDKLVNIVDDLVECVKENSSKDLKKSFKSPEPRLFTPEEFF

RIFNRSIDAFKDFVVASETSDCVVSSTLSPEKDSRVSVTKPFMLPPV

A
```

SEQ ID NO. 15: Nucleotide Sequence Encoding Human Soluble SCF (164 aa and 25 aa N-Terminal Signal Peptide)

```
ATGAAGAAGACACAAACTTGGATTCTCACTTGCATTTATCTTCAGCT

GCTCCTATTTAATCCTCTCGTCAAAACTGAAGGGATCTGCAGGAATC

GTGTGACTAATAATGTAAAAGACGTCACTAAATTGGTGGCAAATCTT

CCAAAAGACTACATGATAACCCTCAAATATGTCCCCGGGATGGATGT

TTTGCCAAGTCATTGTTGGATAAGCGAGATGGTAGTACAATTGTCAG

ACAGCTTGACTGATCTTCTGGACAAGTTTTCAAATATTTCTGAAGGC

TTGAGTAATTATTCCATCATAGACAAACTTGTGAATATAGTGGATGA

CCTTGTGGAGTGCGTGAAAGAAAACTCATCTAAGGATCTAAAAAAT

CATTCAAGAGCCCAGAACCCAGGCTCTTTACTCCTGAAGAATTCTTT

AGAATTTTTAATAGATCCATTGATGCCTTCAAGGACTTTGTAGTGGC

ATCTGAAACTAGTGATTGTGTGGTTTCTTCAACATTAAGTCCTGAGA

AAGATTCCAGAGTCAGTGTCACAAAACCATTTATGTTACCCCCTGTT

GCA
```

Any patents or publications mentioned in this specification are incorporated herein by reference to the same extent as if each individual publication is specifically and individually indicated to be incorporated by reference.

The transgenic animals, compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A transgenic immunodeficient non-obese diabetic (NOD) mouse homozygous for the scid mutation and having an IL2 receptor gamma chain deficiency, whose genome comprises a nucleic acid encoding xenogeneic Stem Cell Factor operably linked to a promoter, wherein the animal expresses the xenogeneic Stem Cell Factor, with the proviso that no exogenous GM-CSF is expressed in the transgenic immunodeficient mouse, wherein administration of human stem cells to the mouse in the absence of conditioning by irradiation prior to administration of the human stem cells results in similar or greater levels of engraftment of the human stem cells compared to a non-obese diabetic (NOD) mouse homozygous for the scid mutation and having an IL2 receptor gamma chain deficiency which is conditioned by irradiation prior to administration of human stem cells and which does not express the xenogeneic Stem Cell Factor.

2. The transgenic mouse of claim 1, wherein the xenogeneic Stem Cell Factor is selected from the group consisting of: human membrane-associated stem cell factor 248 ($SCF^{248}$), human membrane-associated stem cell factor 220 ($SCF^{220}$) and human soluble stem cell factor (sSCF).

3. The transgenic mouse of claim 1, wherein the xenogeneic Stem Cell Factor comprises an amino acid sequence selected from the group consisting of: SEQ ID NO. 1, SEQ ID NO. 3, SEQ ID NO. 14, Stem Cell Factor encoded by the complement of a nucleic acid which hybridizes to SEQ ID No. 2 under highly stringent hybridization conditions, Stem Cell Factor encoded by the complement of a nucleic acid which hybridizes to SEQ ID No. 4 under highly stringent hybridization conditions and Stem Cell Factor encoded by the complement of a nucleic acid which hybridizes to SEQ ID No. 15 under highly stringent hybridization conditions, wherein highly stringent hybridization conditions are hybridization in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes.

4. The transgenic mouse of claim 1, wherein the transgenic animal is a NOD.Cg-Prkdc$^{scid}$ Il2rg$^{tm1Wjl}$/SzJ mouse whose genome comprises a nucleic acid encoding a xenogeneic Stem Cell Factor operably linked to a promoter, wherein the mouse expresses a xenogeneic Stem Cell Factor.

5. The transgenic mouse of claim 1, further comprising xenogeneic haematopoietic stem cells.

6. The transgenic mouse of claim 1, further comprising xenogeneic leukocytes.

7. A method for xenogeneic stem cell engraftment in an immunodeficient non-obese diabetic (NOD) mouse homozygous for the scid mutation, having an IL2 receptor gamma chain deficiency and having a severe combined immunodeficiency, comprising:
administering xenogeneic stem cells to the immunodeficient mouse in absence of conditioning of the mouse by irradiation; and
delivering xenogeneic Stem Cell Factor to the xenogeneic stem cells in the immunodeficient mouse, with the proviso that no GM-CSF is administered to mobilize stem cells in the mouse.

8. The method of claim 7, wherein the immunodeficient mouse comprises a nucleic acid encoding xenogeneic Stem Cell Factor operably linked to a promoter, wherein the animal expresses a xenogeneic Stem Cell Factor.

9. The method of claim 7, wherein the xenogeneic stem cells and the xenogeneic Stem Cell Factor are derived from the same species.

10. The method of claim 7, wherein the xenogeneic Stem Cell Factor is selected from the group consisting of: human membrane-associated stem cell factor 248 ($SCF^{248}$), human membrane-associated stem cell factor 220 ($SCF^{220}$) and soluble stem cell factor (sSCF).

11. The method of claim 7, wherein the xenogeneic Stem Cell Factor comprises an amino acid sequence selected from the group consisting of: SEQ ID NO. 1, SEQ ID NO. 3, SEQ ID NO. 14, Stem Cell Factor encoded by the complement of a nucleic acid which hybridizes to SEQ ID No. 2 under highly stringent hybridization conditions, Stem Cell Factor encoded by the complement of a nucleic acid which hybridizes to SEQ ID No. 4 under highly stringent hybridization conditions and Stem Cell Factor encoded by the complement of a nucleic acid which hybridizes to SEQ ID No. 15 under highly stringent hybridization conditions, wherein highly stringent hybridization conditions are hybridization in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes.

12. The method of claim 7, wherein the immunodeficient mouse is a NOD.Cg-Prkdc$^{scid}$ Il2rg$^{tm1Wjl}$/SzJ mouse whose genome comprises a nucleic acid encoding a xenogeneic Stem Cell Factor operably linked to a promoter, wherein the mouse expresses a xenogeneic Stem Cell Factor.

13. The method of claim 12, wherein the xenogeneic Stem Cell Factor is selected from the group consisting of: human membrane-associated stem cell factor 248 ($SCF^{248}$), human membrane-associated stem cell factor 220 ($SCF^{220}$) and soluble stem cell factor (sSCF).

14. The method of claim 7, wherein the immunodeficient mouse is not irradiated prior to administering the xenogeneic stem cells.

15. The method of claim 7, wherein the immunodeficient mouse is not conditioned by administration of a radiomimetic agent prior to administering the xenogeneic stem cells.

16. A method for xenogeneic stem cell engraftment in a NOD.Cg-Prkdc$^{scid}$ Il2rg$^{tm1Wjl}$/SzJ mouse whose genome comprises a nucleic acid encoding a xenogeneic Stem Cell Factor operably linked to a promoter, wherein the mouse expresses the xenogeneic Stem Cell Factor, comprising:
administering xenogeneic stem cells to the mouse without conditioning the mouse by irradiation.

* * * * *

SEQUENCE LISTING

```
<160> NUMBER OF SEQ ID NOS: 15

<210> SEQ ID NO 1
<211> LENGTH: 245
<212> TYPE: PRT
<213> ORGANISM: Homo sapiens

<400> SEQUENCE: 1

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60
```

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Leu Val
            100                 105                 110

Glu Cys Val Lys Glu Asn Ser Ser Lys Asp Leu Lys Lys Ser Phe Lys
            115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Gly Lys Ala
                165                 170                 175

Lys Asn Pro Pro Gly Asp Ser Ser Leu His Trp Ala Ala Met Ala Leu
            180                 185                 190

Pro Ala Leu Phe Ser Leu Ile Ile Gly Phe Ala Phe Gly Ala Leu Tyr
            195                 200                 205

Trp Lys Lys Arg Gln Pro Ser Leu Thr Arg Ala Val Glu Asn Ile Gln
210                 215                 220

Ile Asn Glu Glu Asp Asn Glu Ile Ser Met Leu Gln Gly Lys Glu Arg
225                 230                 235                 240

Glu Phe Gln Glu Val
            245

<210> SEQ ID NO 2
<211> LENGTH: 738
<212> TYPE: DNA
<213> ORGANISM: Homo sapiens

<400> SEQUENCE: 2
atgaagaaga cacaaacttg gattctcact tgcatttatc ttcagctgct cctatttaat      60
cctctcgtca aaactgaagg gatctgcagg aatcgtgtga ctaataatgt aaaagacgtc     120
actaaattgg tggcaaatct tccaaaagac tacatgataa ccctcaaata tgtccccggg     180
atggatgttt tgccaagtca ttgttggata agcgagatgg tagtacaatt gtcagacagc     240
ttgactgatc ttctggacaa gttttcaaat atttctgaag gcttgagtaa ttattccatc     300
atagacaaac ttgtgaatat agtggatgac cttgtggagt gcgtgaaaga aaactcatct     360
aaggatctaa aaaatcatt caagagccca gaacccaggc tctttactcc tgaagaattc     420
tttagaattt ttaatagatc cattgatgcc ttcaaggact tgtagtggc atctgaaact     480 agtgattgtg tggtttcttc aacattaagt cctgagaaag ggaaggccaa aaatccccct     540
ggagactcca gcctcactg gcagccatg gcattgccag cattgtttc tcttataatt     600 ggctttgctt ttggagcctt atactggaag aagagacagc caagtcttac aagggcagtt     660
gaaaatatac aaattaatga agaggataat gagataagta tgttgcaaga gaaagagaga     720
gagtttcaag aagtgtaa                                                  738

<210> SEQ ID NO 3
<211> LENGTH: 273
<212> TYPE: PRT
<213> ORGANISM: Homo sapiens

<400> SEQUENCE: 3

Met Lys Lys Thr Gln Thr Trp Ile Leu Thr Cys Ile Tyr Leu Gln Leu

```
                  1               5                  10                 15
Leu Leu Phe Asn Pro Leu Val Lys Thr Glu Gly Ile Cys Arg Asn Arg
                 20                  25                 30
Val Thr Asn Asn Val Lys Asp Val Thr Lys Leu Val Ala Asn Leu Pro
                 35                  40                 45
Lys Asp Tyr Met Ile Thr Leu Lys Tyr Val Pro Gly Met Asp Val Leu
 50                  55                 60
Pro Ser His Cys Trp Ile Ser Glu Met Val Val Gln Leu Ser Asp Ser
 65                  70                 75                 80
Leu Thr Asp Leu Leu Asp Lys Phe Ser Asn Ile Ser Glu Gly Leu Ser
                 85                  90                 95
Asn Tyr Ser Ile Ile Asp Lys Leu Val Asn Ile Val Asp Asp Leu Val
                100                 105                110
Glu Cys Val Lys Glu Asn Ser Ser Lys Asp Leu Lys Lys Ser Phe Lys
                115                 120                125
Ser Pro Glu Pro Arg Leu Phe Thr Pro Glu Gly Phe Phe Arg Ile Phe
                130                 135                140
Asn Arg Ser Ile Asp Ala Phe Lys Asp Phe Val Val Ala Ser Glu Thr
145                 150                 155                160
Ser Asp Cys Val Val Ser Ser Thr Leu Ser Pro Glu Lys Asp Ser Arg
                165                 170                175
Val Ser Val Thr Lys Pro Phe Met Leu Pro Pro Val Ala Ala Ser Ser
                180                 185                190
Leu Arg Asn Asp Ser Ser Ser Asn Arg Lys Ala Lys Asn Pro Pro
                195                 200                205
Gly Asp Ser Ser Leu His Trp Ala Ala Met Ala Leu Pro Ala Leu Phe
                210                 215                220
Ser Leu Ile Ile Gly Phe Ala Phe Gly Ala Leu Tyr Trp Lys Lys Arg
225                 230                 235                240
Gln Pro Ser Leu Thr Arg Ala Val Glu Asn Ile Gln Ile Asn Glu Glu
                245                 250                255
Asp Asn Glu Ile Ser Met Leu Gln Glu Lys Glu Arg Glu Phe Gln Glu
                260                 265                270
Val

<210> SEQ ID NO 4
<211> LENGTH: 822
<212> TYPE: DNA
<213> ORGANISM: Homo sapiens

<400> SEQUENCE: 4
atgaagaaga cacaaacttg gattctcact tgcatttatc ttcagctgct cctatttaat       60
cctctcgtca aaactgaagg gatctgcagg aatcgtgtga ctaataatgt aaaagacgtc      120
actaaattgg tggcaaatct tccaaaagac tacatgataa ccctcaaata tgtccccggg      180
atggatgttt tgccaagtca ttgttggata agcgagatgg tagtacaatt gtcagacagc      240
ttgactgatc ttctggacaa gttttcaaat atttctgaag cttgagtaa ttattccatc       300 atagacaaac ttgtgaatat agtggatgac cttgtggagt gcgtgaaaga aaactcatct      360
aaggatctaa aaaatcatt caagagccca gaacccaggc tctttactcc tgaagaattc       420
tttagaattt ttaatagatc cattgatgcc ttcaaggact tgtagtggc atctgaaact       480 agtgattgtg tggtttcttc aacattaagt cctgagaaag attccagagt cagtgtcaca      540
aaaccattta tgttacccc tgttgcagcc agctcccta ggaatgacag cagtagcagt        600
```

-continued

| | |
|---|---|
| aataggaagg ccaaaaatcc ccctggagac tccagcctac actgggcagc catggcattg | 660 |
| ccagcattgt tttctcttat aattggcttt gcttttggag ccttatactg aagaagaga | 720 |
| cagccaagtc ttacaagggc agttgaaaat atacaaatta atgaagagga taatgagata | 780 |
| agtatgttgc aagagaaaga gagagagttt caagaagtgt aa | 822 |

<210> SEQ ID NO 5
<211> LENGTH: 1405
<212> TYPE: DNA
<213> ORGANISM: Homo sapiens

<400> SEQUENCE: 5

| | |
|---|---|
| ccgcctcgcg ccgagactag aagcgctgcg ggaagcaggg acagtggaga gggcgctgcg | 60 |
| ctcgggctac ccaatgcgtg gactatctgc cgccgctgtt cgtgcaatat gctggagctc | 120 |
| cagaacagct aaacggagtc gccacaccac tgtttgtgct ggatcgcagc gctgcctttc | 180 |
| cttatgaaga agacacaaac ttggattctc acttgcattt atcttcagct gctcctattt | 240 |
| aatcctctcg tcaaaactga agggatctgc aggaatcgtg tgactaataa tgtaaaagac | 300 |
| gtcactaaat tggtggcaaa tcttccaaaa gactacatga taaccctcaa atatgtcccc | 360 |
| gggatggatg ttttgccaag tcattgttgg ataagcgaga tggtagtaca attgtcagac | 420 |
| agcttgactg atcttctgga caagttttca aatatttctg aaggcttgag taattattcc | 480 |
| atcatagaca aacttgtgaa tatagtggat gaccttgtgg agtgcgtgaa agaaaactca | 540 |
| tctaaggatc taaaaaaatc attcaagagc ccagaaccca ggctctttac tcctgaagaa | 600 |
| ttctttagaa ttttttaatag atccattgat gccttcaagg actttgtagt ggcatctgaa | 660 |
| actagtgatt gtgtggtttc ttcaacatta agtcctgaga agattccag agtcagtgtc | 720 |
| acaaaaccat ttatgttacc ccctgttgca gccagctccc ttaggaatga cagcagtagc | 780 |
| agtaatagga aggccaaaaa tccccctgga gactccagcc tacactgggc agccatggca | 840 |
| ttgccagcat tgttttctct tataattggc tttgcttttg gagccttata ctggaagaag | 900 |
| agacagccaa gtcttacaag ggcagttgaa aatatacaaa ttaatgaaga ggataatgag | 960 |
| ataagtatgt tgcaagagaa agagagagag tttcaagaag tgtaaattgt ggcttgtatc | 1020 |
| aacactgtta ctttcgtaca ttggctggta acagttcatg tttgcttcat aaatgaagca | 1080 |
| gctttaaaca aattcatatt ctgtctggag tgacagacca catctttatc tgttcttgct | 1140 |
| acccatgact ttatatggat gattcagaaa ttggaacaga atgttttact gtgaaactgg | 1200 |
| cactgaatta atcatctata aagaagaact tgcatggagc aggactctat tttaaggact | 1260 |
| gcgggacttg ggtctcattt agaacttgca gctgatgttg aagagaaag cacgtgtctc | 1320 |
| agactgcatg taccatttgc atggctccag aaatgtctaa atgctgaaaa aacacctagc | 1380 |
| tttattcttc agatacaaac tgcag | 1405 |

<210> SEQ ID NO 6
<211> LENGTH: 20
<212> TYPE: DNA
<213> ORGANISM: artificial
<220> FEATURE:
<223> OTHER INFORMATION: primer for human phosphoglycerate kinase (PGK) promoter

<400> SEQUENCE: 6

| | |
|---|---|
| acattcttac gtccgttcgc | 20 |

<210> SEQ ID NO 7
<211> LENGTH: 20

```
<212> TYPE: DNA
<213> ORGANISM: artificial
<220> FEATURE:
<223> OTHER INFORMATION: primer for human phosphoglycerate kinase (PGK)
      promoter

<400> SEQUENCE: 7
actagtgaga cgtgcggctt                                              20

<210> SEQ ID NO 8
<211> LENGTH: 26
<212> TYPE: DNA
<213> ORGANISM: artificial
<220> FEATURE:
<223> OTHER INFORMATION: primer for human stem cell factor

<400> SEQUENCE: 8
ccaaaagact acatgataac cctcaa                                       26

<210> SEQ ID NO 9
<211> LENGTH: 21
<212> TYPE: DNA
<213> ORGANISM: artificial
<220> FEATURE:
<223> OTHER INFORMATION: primer for human stem cell factor

<400> SEQUENCE: 9
ccatctcctt atccaacaat g                                            21

<210> SEQ ID NO 10
<211> LENGTH: 18
<212> TYPE: DNA
<213> ORGANISM: artificial
<220> FEATURE:
<223> OTHER INFORMATION: primer for apolipoprotein B

<400> SEQUENCE: 10
cacgtgggct ccagcatt                                                18

<210> SEQ ID NO 11
<211> LENGTH: 22
<212> TYPE: DNA
<213> ORGANISM: artificial
<220> FEATURE:
<223> OTHER INFORMATION: primer for apolipoprotein B

<400> SEQUENCE: 11
tcaccagtca tttctgcctt tg                                           22

<210> SEQ ID NO 12
<211> LENGTH: 22
<212> TYPE: DNA
<213> ORGANISM: artificial
<220> FEATURE:
<223> OTHER INFORMATION: probe for apolipoprotein B

<400> SEQUENCE: 12
ccaatggtcg ggcactgctc aa                                           22

<210> SEQ ID NO 13
<211> LENGTH: 23
<212> TYPE: DNA
<213> ORGANISM: artificial
<220> FEATURE:
<223> OTHER INFORMATION: probe for stem cell factor

<400> SEQUENCE: 13
```

```
cttggcaaaa catccatccc ggg                                                23
```

<210> SEQ ID NO 14
<211> LENGTH: 189
<212> TYPE: PRT
<213> ORGANISM: Homo sapiens
<400> SEQUENCE: 14

```
Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala
            180                 185
```

<210> SEQ ID NO 15
<211> LENGTH: 567
<212> TYPE: DNA
<213> ORGANISM: Homo sapiens
<400> SEQUENCE: 15

```
atgaagaaga cacaaacttg gattctcact tgcatttatc ttcagctgct cctatttaat     60
cctctcgtca aaactgaagg gatctgcagg aatcgtgtga ctaataatgt aaaagacgtc    120
actaaattgg tggcaaatct tccaaaagac tacatgataa ccctcaaata tgtccccggg    180
atggatgttt tgccaagtca ttgttggata agcgagatgg tagtacaatt gtcagacagc    240
ttgactgatc ttctggacaa gttttcaaat atttctgaag gcttgagtaa ttattccatc    300
atagacaaac ttgtgaatat agtggatgac cttgtggagt gcgtgaaaga aaactcatct    360
aaggatctaa aaaatcatt caagagccca gaacccaggc tctttactcc tgaagaattc    420
tttagaattt ttaatagatc cattgatgcc ttcaaggact tgtagtggc atctgaaact    480 agtgattgtg tggtttcttc aacattaagt cctgagaaag attccagagt cagtgtcaca    540
aaaccattta tgttaccccc tgttgca                                        567
```